US008772026B2

(12) United States Patent
Chen et al.

(10) Patent No.: US 8,772,026 B2
(45) Date of Patent: Jul. 8, 2014

(54) ENHANCEMENT OF IMMUNE RESPONSES BY 4-1 BB-BINDING AGENTS

(75) Inventors: Lieping Chen, Hamden, CT (US); Scott E. Strome, Reisterstown, MD (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 79 days.

(21) Appl. No.: 13/426,151

(22) Filed: Mar. 21, 2012

(65) Prior Publication Data

US 2012/0225043 A1 Sep. 6, 2012

Related U.S. Application Data

(63) Continuation of application No. 12/614,150, filed on Nov. 6, 2009, now Pat. No. 8,163,550, which is a continuation of application No. 10/492,056, filed as application No. PCT/US02/32364 on Oct. 9, 2002, now Pat. No. 7,651,686.

(60) Provisional application No. 60/328,004, filed on Oct. 9, 2001.

(51) Int. Cl.
*C12N 5/00* (2006.01)
(52) U.S. Cl.
USPC .......................................................... 435/325
(58) Field of Classification Search
None
See application file for complete search history.

(56) References Cited

U.S. PATENT DOCUMENTS

| 4,257,774 | A | 3/1981 | Richardson et al. |
| 4,946,778 | A | 8/1990 | Ladner et al. |
| 5,674,704 | A | 10/1997 | Goodwin et al. |
| 5,874,240 | A | 2/1999 | Ni et al. |
| 5,928,893 | A | 7/1999 | Kang et al. |
| 6,210,669 | B1 | 4/2001 | Aruffo et al. |
| 6,297,008 | B1 | 10/2001 | Okamoto et al. |
| 6,303,121 | B1 | 10/2001 | Kwon |
| 6,355,779 | B1 | 3/2002 | Goodwin et al. |
| 6,458,934 | B1 | 10/2002 | Hong et al. |
| 7,651,686 | B2 | 1/2010 | Chen et al. |
| 2002/0076409 | A1* | 6/2002 | March et al. ................ 424/145.1 |
| 2002/0119121 | A1* | 8/2002 | Vitiello et al. ................ 424/85.2 |
| 2002/0160973 | A1* | 10/2002 | Pero et al. ........................ 514/44 |
| 2002/0168719 | A1 | 11/2002 | Kwon |
| 2002/0177551 | A1* | 11/2002 | Terman ............................. 514/12 |
| 2003/0223989 | A1 | 12/2003 | Pluenneke |
| 2004/0247563 | A1 | 12/2004 | Lynch et al. |
| 2005/0013811 | A1 | 1/2005 | Chen et al. |

FOREIGN PATENT DOCUMENTS

| WO | WO 96/29348 | 9/1996 | |
| WO | WO 98/16249 | 4/1998 | |
| WO | WO 98/36096 | 8/1998 | ............ C12Q 1/68 |
| WO | WO 99/36093 | 7/1999 | ............ A61K 39/395 |
| WO | WO 00/29445 | 5/2000 | |
| WO | WO 00/29582 | 5/2000 | ............ C12N 15/12 |
| WO | WO 00/41508 | 7/2000 | |
| WO | WO 01/62905 | 8/2001 | |
| WO | WO 03/006632 | 1/2003 | ............ C12N 5/00 |
| WO | WO 03/049755 | 6/2003 | |

OTHER PUBLICATIONS

Cannons et al., (J. Immunol., 2001, 167: 1313-1324).*
Strome et al., (J. Immunotherapy., 2000, 23: 430-437).*
Adachi et al., "Aberrant transcription caused by the insertion of an early transposable element in an intron of the Fas antigen gene of lpr mice," Proc. Natl. Acad. Sci. USA, 1993, 90:1756-1760.
Alderson et al., "Molecular and biological characterization of human 4-1BB and its ligand," Eur. J. Immunol., 1994, 24:2219-2227.
Anukam et al., "Augmentation of antimicrobial metronidazole therapy of bacterial vaginosis with oral probiotic *Lactobacillus rhamnosus* GR-1 and *Lactobacillus reuteri* RC-14: randomized, double-blind, placebo controlled trial," Microbes and Infection, 2006, pp. 1-5.
BD PharmingenTM Technical Data Sheet, "Purified Rat Anti-Mouse Ly-6G (Gr-1) Monoclonal Antibody for Immunohistochemistry (IHC)" 2003, 1 page.
Blazar et al., "Infusion of anti-B7.1 (CD80) and anti-B7.2 (CD86) monoclonal antibodies inhibits murine graft-versus-host disease lethality in part via direct effects on CD4+ and CD8+ T cells," J. Immunol., 1996, 157:3250-3259.
Cairns et al., "Immortalization of multipotent growth-factor dependent hemopoietic progenitors from mice transgenic for GATA-1 driven SV40 tsA58 gene," EMBO J., 1994, 13:4577-4586.
Cohen et al., "Lpr and gld: Single Gene Models of Systemic Autoimmunity and Lymphoproliferative Disease," Annu. Rev. Immunol., 1991, 9:243-269.
Cole et al., "The EBV-Hybridoma Technique and its Application to Human Lung Cancer," Monoclonal Antibodies and Cancer Therapy, 1983, Alan R. Liss, Inc., pp. 77-96.
Cote et al., "Generation of human monoclonal antibodies reactive with cellular antigens," Proc. Natl. Acad. Sci USA, 1983, 80:2026.
Ding et al., "Release of Reactive Nitrogen Intermediates and Reactive Oxygen Intermediates from Mouse Peritoneal Macrophages," J. Immunol., 1988, 141:2407-2412.
Finck et al., "Treatment of Murine Lupus with CTLA4Ig," Science, 1994, 265:1225-1227.
Fleming et al., "Selective Expression of Ly-6G on Myeloid Lineage Cells in Mouse Bone Marrow," J. Immunol., 1993, 151:2399-2408.
Foell et al., "CD137 costimulatory T cell receptor engagement reverses acute disease in lupus-prone NZB x NZW F1 mice," J. Clin. Invest., 2003, 10:1505-1518.

(Continued)

Primary Examiner — Ilia Ouspenski
(74) Attorney, Agent, or Firm — Fish & Richardson P.C.

(57) ABSTRACT

This invention features methods of enhancing immune responses in mammalian subjects and in vitro methods of enhancing the response of a T cell. Also embodied by the invention are methods of receiving and preventing the induction of energy in T cells.

18 Claims, 18 Drawing Sheets

(56) References Cited

OTHER PUBLICATIONS

Foell et al., "CD137-Mediated T Cell Co-Stimulation Terminates Existing Autoimmune Disease in SLE-Prone NZB/NZW F1 Mice," Ann. N.Y. Acad. Sci., 2003, 987:230-235.
Goodwin et al., "Molecular cloning of a ligand for the inducible T cell gene 4-1BB: a member of an emerging family of cytokines with homology to tumor necrosis factor," Eur. J. Immunol., 1993, 23:2631-2641.
Haendeler et al., "Nitric Oxide and Apoptosis," Vitam. Horm., 1999, 57:49-77.
Hestdal et al., "Characterization and Regulation of RB6-8C5 Antigen Expression on Murine Bone Marrow Cells," J. Immunol., 1991, 147:22-28.
Hoffman, "T Cells in the Pathogenesis of Systemic Lupus Erythematosus," Front. Biosci., 2001, 6:D1369-1378.
Hunter, "Diabetes in pregnancy," Effective Care in Pregnancy and Childbirth, vol. 1, 1989, Chalmers et al. (eds.), Oxford University Press, pp. 578-593.
Huse et al., "Generation of a Large Combinatorial Library of the Immunoglobulin Repertoire in Phage Lambda," Science, 1989, 246:1275.
Jacobson et al., "Unique site of IgG2a and rheumatoid factor production in MRL/Ipr mice," Immunol. Rev., 1997, 156:103-110.
Kaliyaperumal et al., "Antigen-Specific Therapy of Murine Lupus Nephritis Using Nucleosomal Peptides: Tolerance Spreading Impairs Pathogenic Function of Autoimmune T and B Cells," J. Immunol., 1999, 162:5775-5783.
Kalled et al., "Anti-CD40 Ligand Antibody Treatment of SNF1 Mice with Established Nephritis: Preservation of Kidney Function," J. Immunol., 1998, 160:2158-2165.
Kelley et al., "Cytokines in the Pathogenesis of Systemic Lupus Erythematosus," Semin. Nephrol., 1999, 19:57-66.
Köhler et al., "Continuous cultures of fused cells secreting antibody of predefined specificity," Nature, 1975, 256:495-497.
Kozbor et al., "The production of monoclonal antibodies from human lymphocytes," Immunology Today, 1983, 4:72.
Kusmartsev et al., "Gr-1+ myeloid cells derived from tumor-bearing mice inhibit primary T cell activation induced through CD3/CD28 costimulation," J. Immunol., 2000, 165:779-785.
Kwon et al., "4-1BB: Still in the Midst of Darkness," Mol. Cells, 2000, 10:119-126.
Lawson et al., "Treatment of murine lupus with cDNA encoding IFN-γR/Fc," J. Clin. Invest., 2000, 106:207-215.
Lenardo et al., "Mature T Lymphocyte Apoptosis—Immune Regulation in a Dynamic and Unpredictable Antigenic Environment," Annu. Rev. Immunol., 1999, 17:221-253.
Liang et al., "Autoantibody Responses and Pathology Regulated by B7-1 and B7-2 Costimulation in MRL/Ipr Lupus," J. Immunol., 2000, 165:3436-3443.
Melero et al., "NK1.1 Cells Express 4-1BB (CDw137) Costimulatory Molecule and Are Required for Tumor Immunity Elicited by Anti-4-1BB Monoclonal Antibodies," Cellular Immunology, 1998, 190:167-172.
Merrill, "Emergence of targeted immune therapies for systemic lupus," Expert Opin. Emerging Drugs, 2005, 10:53-65.
Mohan et al., "Interaction Between CD40 and Its Ligand gp39 in the Development of Murine Lupus Nephritis," J. Immunol., 1995, 154:1470-1480.
Morse et al., "Abnormalities Induced by the Mutant Gene Ipr: Expansion of a Unique Lymphocyte Subset," J. Immunol., 1982, 129:2612-2615.
Pollok et al., "4-1BB T-cell antigen binds to mature B cells and macrophages, and costimulates anti-μ-primed splenic B cells," Eur. J. Immunol., 1994, 24:367-374.
Pollok et al., "Inducible T Cell Antigen 4-1BB," J. Immunol., 1993, 150:771-781.
Porter, "The hydrolysis of rabbit γ-globulin and antibodies with crystalline papain," Biochem. J., 1959, 73:119-126.

Salih et al., "4-1BB ligand—just another costimulating molecule?" International Journal of Clinical Pharmacology and Therapeutics, 2002, 40:348-353.
Samulski, "Targeted integration of adenoassociated cirus (AAV) into human chromosome 19," EMBO J., 1991, 10: 3941-3950.
Shaknovich et al., "The promyelocytic leukemia zinc finger protein affects myeloid cell growth, differentiation, and apoptosis," Mol. Cell. Biol., 1998, 18:5533-5545.
Sneller et al., "A novel lymphoproliferative/autoimmune syndrome resembling murine Ipr/gld disease," J. Clin. Invest., 1992, 90:334-341.
Sorge et al., "Amphotropic retrovirus vector system for human cell gene transfer," Molec. Cell. Biol., 1984,4: 1730-1737.
Suda et al., "Why do defects in the Fas-Fas ligand system cause autoimmunity?" J. Allergy Clin. Immunol., 1997, 100:597-101.
Sun et al., "Administration of Agonistic Anti-4-1BB Monoclonal Antibody Leads to the Amelioration of Experimental Autoimmune Encephalomyelitis," J. Immunol., 2002, 168:1457-1465.
Sun et al., "Costimulatory molecule-targeted antibody therapy of a spontaneous autoimmune disease," Nature Medicine, 2002, 8(12):1405-1413.
Sun et al., "Signaling of 4-1BB Leads to Amelioration of Experimental Autoimmune Encephalomyelitis," FASEB J., 2001, vol. 5, p. A1210 Abstract 950.9.
Theofilopoulos et al., "Tumour necrosis factor and other cytokines in murine lupus," Ann. Rheum. Dis., 1999, 58 Suppl. 1:149-55.
Vinay et al., "Role of 4-1BB in immune responses," Semin. Immunol., 1998, 10(6):481-489.
Wang et al., "Ligand binding sites of inducible costimulator and high avidity mutants with improved function," J. Exp. Med., 2002, 195:1033-1041.
Williams et al., "Introduction of foreign genes into tissues of living mice by DNA-coated microprojectiles," Proc. Natl. Proc. Sci. USA, 1991,38:2726.
Williams et al., "Nitric Oxide Synthase Plays a Signaling Role in TCR-Triggered Apoptotic Death," J. Immunol., 1998, 161:6526-6531.
Wofsy et al., "The Proliferating Cells in Autoimmune MRL/Ipr Mice Lack L3T4, an Antigen on "Helper" T Cells that Is Involved in the Response to Class II Major Histocompatibility Antigens," J. Immunol., 1984, 132:2686-2689.
Wofsy, "Treatment of Murine Lupus with Anti-CD4 Monoclonal Antibodies," Immunol. Ser., 1993, 59:221-236.
International Search Report for PCT/US2002/32364, mailed Mar. 25, 2003, 2 pages.
European Search Report for Application No. EP 02802551, 3 pages, completed Oct. 14, 2004.
Bubenik, "Genetically engineered dendritic cell-based cancer vaccines (Review)", Int. J. Oncol., 18:475-478 (2001).
Diehl et al., "In Vivo Triggering Through 4-1BB Enables Th Independent Priming of CTL in the Presence of an Intact CD28 Costimulatory Pathway", J. Immunol., 168 (8):3755-3762 (2002).
Guinn et al., "4-1BBL Cooperates with B7-1 and B7-2 in Converting a B Cell Lymphoma Cell Line into a Long-Lasting Antitumor Vaccine", J. Immunol., 162 (8):5003-5010 (1999).
Hellstrom et al., T Cell immunity to Tumor Antigens, Critical Reviews in Immunology, 18:1-6 (1998).
Huang Z., Structural chemistry and therapeutic intervention of protein-protein interactions in immune response, human immunodeficiency virus entry, and apoptosis, Pharmacology and Therapeutics, 86:201-215 (2000).
Kim et al., State-of-the-Art Review: Therapeutic Potential of 4-1BB (CD137) As a Regulator for Effector CD8+ T Cells., J. Hematotherapy & Stem Cell Res., 10:441-449 (Aug. 2001).
Melero et al., "Monoclonal antibodies against the 4-1BB T-cell activation molecule eradicate established tumors", Nat. Med., 6(3):682-685 (1997).
Melero et al., "Amplification of tumor immunity by gene transfer of the co-stimulatory 4-1BB ligand: synergy with the CD28 co-stimulatory pathway", Eur. J. Immunol., 28:1116-1121 (1998).
Melief et al., "Strategies for Immunotherapy of Cancer", Advances in Immunology, Academic Press Inc., NY, NY 75:235-282 (2000).

(56) References Cited

OTHER PUBLICATIONS

Sica et al., Biochemical and Immunological Characteristics of 4-1BB (CD137) Receptor and Ligand and Potential Applications in Cancer Therapy, Archivum Immunologiae et Therapiae Experimentalis, 47:275-279 (1999).

Takahashi et al., "Cutting Edge: 4-1BB is a Bona Fide CD8 T Cell Survival Signal", J. Immunol., 162(9): 5037-5040 (1999).

Ueda et al., Sequence-specific DNA damage induced by reduced mitomycin C and 7-N-(p-hydroxyphenyl)mitomycin C. Nucleic Acids Res. 12:6673-6683 (1984).

Wilcox et al., "Provision of antigen and CD137 signaling breaks immunological ignorance, promoting regression of poorly immunogenic tumors", J. Clin. Invest., 19(5):651-659 (2002).

* cited by examiner

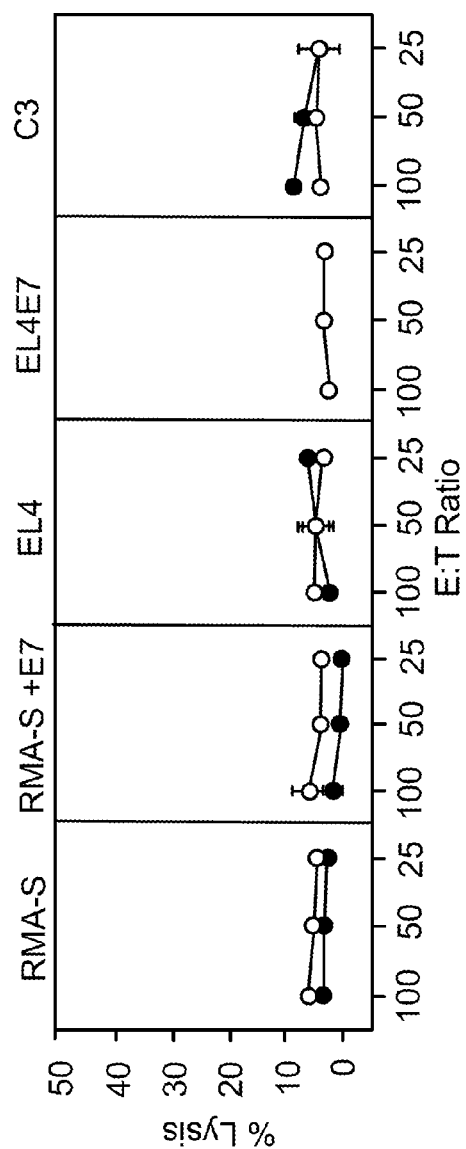
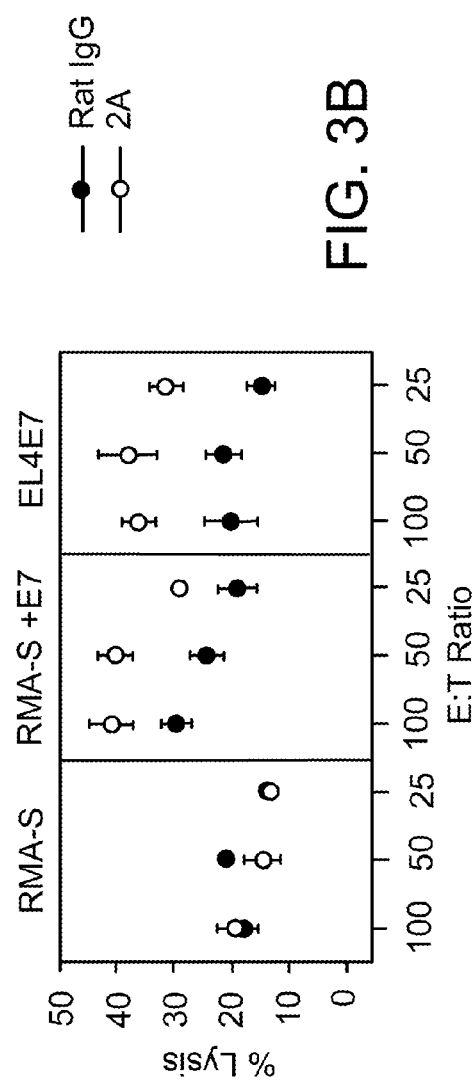
FIG. 3A
FIG. 3B

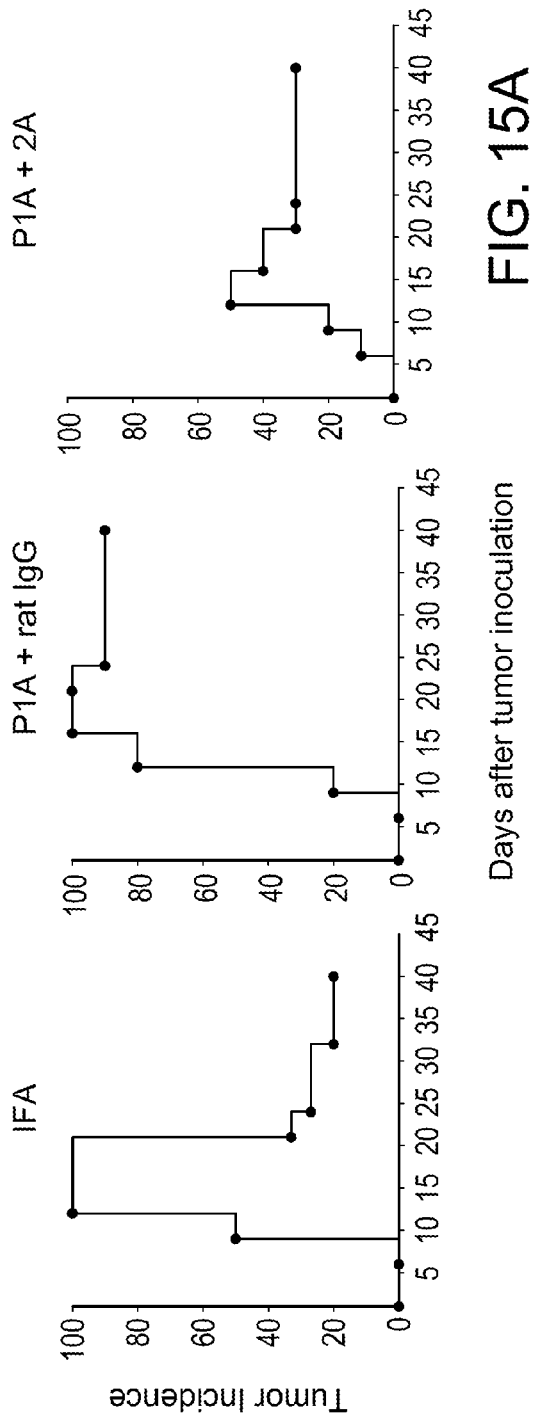
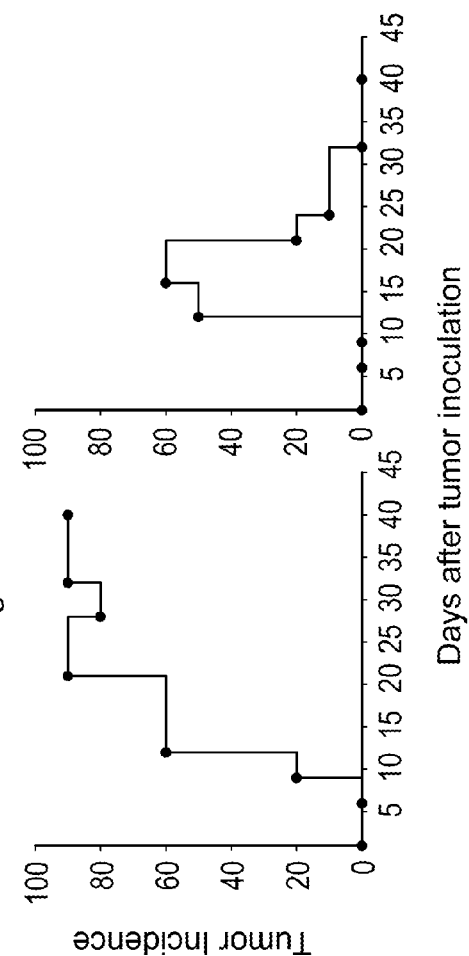
FIG. 15A
FIG. 15B

ENHANCEMENT OF IMMUNE RESPONSES BY 4-1 BB-BINDING AGENTS

This application is a continuation, and claims priority, of U.S. application Ser. No. 12/614,150, filed Nov. 6, 2009, now U.S. Pat. No. 8,163,550 which is a continuation of U.S. application Ser. No. 10/492,056, having a 371 completion date of Aug. 17, 2004, now U.S. Pat. No. 7,651,686, issued Jan. 26, 2010, which is a U.S. National Stage application, and claims priority of International Application No. PCT/US02/32364, filed Oct. 9, 2002, which claims priority of U.S. Provisional Application Ser. No. 60/328,004, filed Oct. 9, 2001. The contents of all of the prior applications are incorporated herein by reference in their entirety.

This invention was made with government support under grant numbers CA079915, CA085721, and DE000459 awarded by the National Institutes of Health. The government has certain rights in the invention.

TECHNICAL FIELD

This invention relates to immunoregulation, and more particularly to T cell response regulation.

BACKGROUND

Mammalian T lymphocytes recognize antigenic peptides bound to major histocompatibility complex (MHC) molecules on the surface of antigen presenting cells (APC). The antigenic peptides are generated by proteolytic degradation of protein antigens within the APC. The interaction of the T cells with the APC and the subsequent response of the T cells are qualitatively and quantitatively regulated by interactions between cell surface receptors on the T cells with both soluble mediators and ligands on the surface of APC.

SUMMARY

The inventors have discovered that treatment of mice bearing a weakly immunogenic tumor with an agonistic antibody specific for murine 4-1BB (also known as CD137) and a peptide fragment of a polypeptide expressed by the tumor resulted in regression of the tumor. In addition, treatment of mice bearing a second weakly immunogenic tumor with the same 4-1BB antibody and autologous dendritic cells "primed" in vitro with cells of the tumor resulted in regression of the tumor. Moreover, the inventors have found that signaling via cell-surface 4-1BB molecules and providing an immunogenic stimulus (a) prevents induction of anergy in CD8+ T cells and (b) reverses already established anergy in the CD8+ T cells. Thus the invention features a method of enhancing a mammalian immune response that involves administering to a mammalian subject (e.g., a cancer patient) (a) an immunogenic stimulus such as a tumor associated peptide-epitope and (b) an agonistic 4-1BB-binding agent (e.g., a 4-1BB-specific antibody). The invention also features an in vitro method of enhancing the response of a T cell in which a population of cells containing a T cell is incubated with (a) an immunogenic stimulus such as a peptide-epitope from an infectious microorganism and (b) an agonistic 4-1BB-binding agent (e.g., the 4-1BB ligand).

More specifically, the invention features a method of generating an enhanced immune response in a subject. The method involves administering to the subject: (a) an immunogenic stimulus; and (b) an agonistic 4-1BB-binding agent. The subject can be a human, e.g., a human cancer patient. The immune response enhanced can be a response of a T cell, e.g., a CD8+ T cell or a CD4+ T cell.

The invention also embraces an in vitro method of activating a T cell, e.g., a CD8+ T cell or a CD4+ T cell. This method involves: (a) providing a cell sample comprising a T cell; and (b) culturing the cell sample with an immunogenic stimulus and an agonistic 4-1BB-binding agent.

Another aspect of the invention is a method of preventing induction of anergy or of reversing anergy in a T cell; the method includes contacting the T cell with: (a) an immunogenic stimulus; and (b) an agonistic 4-1BB-binding agent. The contacting can be in vitro or the T cell can be in a mammal (e.g. a human). The contacting can include administering to the mammal: (a) the immunogenic stimulus and the agonistic 4-1BB-binding agent; (b) a nucleic acid encoding the immunogenic stimulus and the agonistic 4-1BB-binding agent; (c) the immunogenic stimulus and a nucleic acid encoding the agonistic 4-1BB binding agent; or (d) a nucleic acid encoding the immunogenic stimulus and a nucleic acid encoding the agonistic 4-1BB binding agent. The contacting can alternatively include administering to the mammal a nucleic acid encoding the immunogenic stimulus and a nucleic acid encoding the 4-1BB binding agent, the nucleic acid encoding the immunogenic stimulus and the nucleic acid encoding the 4-1BB binding agent being in the same nucleic acid molecule. Moreover, the method can include administering a cell transfected or transduced with a nucleic acid encoding the immunogenic stimulus or the 4-1BB-binding agent to the mammal, the cell being a cell, or a progeny of a cell, that prior to the transfection or the transduction, was obtained from the mammal.

In the methods of the invention, the agonistic 4-1BB binding agent can be, for example, (1) an antibody that binds to 4-1BB or (2) the natural ligand for 4-1BB (4-1BBL) or a functional fragment thereof. The immunogenic stimulus can be a (a) a tumor-associated antigen (TAA) or (b) a functional fragment of a TAA and it can be a polypeptide. The TAA can be a molecule produced by a leukemia, a lymphoma, a neurological cancer, a melanoma, a breast cancer, a lung cancer, a head and neck cancer, a gastrointestinal cancer, a liver cancer, a pancreatic cancer, a genitourinary cancer, a prostate cancer, a renal cell cancer, a bone cancer, or a vascular cancer cell. The immunogenic stimulus can be a dendritic cell that has a major histocompatibility complex (MHC) molecule with peptide-epitope bound thereto, the peptide-epitope being a fragment of a TAA or a fragment of a polypeptide produced by an infectious microorganism. The MHC molecule can be a MHC class 1 molecule or a MHC class II molecule. The immunogenic stimulus can be also be a hybrid cell, e.g., a fusion product of a tumor cell and a dendritic cell. In addition, the immunogenic stimulus can be a tumor cell, a tumor cell lysate, a TAA, a peptide-epitope of a TAA, or a heat shock protein bound to peptide-epitope of protein expressed by a tumor cell. The immunogenic stimulus can also be a dendritic cell that has been incubated with tumor cells, a tumor cell lysate, a TAA, a peptide-epitope of a TAA, or a heat shock protein bound to peptide-epitope of protein expressed by a tumor cell. Where the immunogenic stimulus is or contains a tumor cell, an APC, or a hybrid cell, the cell can be transfected with or transformed with a nucleic acid encoding a cytokine or a growth factor, e.g., granulocyte macrophage-colony stimulating factor (GM-CSF).

Alternatively, the immunogenic stimulus can be a molecule produced by an infectious microorganism, e.g., a virus such as a retrovirus, a bacterium, a fungus, or a protozoan parasite.

As used herein, an "enhanced immune response" is obtained by administering to a subject an immunogenic stimulus and an agonistic 4-1 BB-binding agent. In the absence of administration of an agonistic 4-1BB-binding agent, an appropriate immunogenic stimulus either stimulates no immune response in the subject or it stimulates an immune response in the subject that is detectably lower than a response stimulated by administration of the immunogenic stimulus and an agonistic 4-1BB-binding agent.

As used herein, an "anergic T cell" or an "anergized T cell" is a T cell whose ability to respond to an immunogenic stimulus, with respect to at least one activity of the T cell, has been partially or completely inhibited. Thus, for example, an anergic or anergized T cell may lack or have a decreased ability to proliferate and produce interleukin-2 in response to an immunogenic stimulus but its ability to produce interferon-γ in response to the immunogenic stimulus may be substantially intact. Alternatively, an anergic or anergized T cell may display a lack or a decrease in all the functional activities elicited by an immunogenic stimulus in such a T cell.

As used herein, "reversing" anergy in a T cell means fully or partially restoring the ability of the T cell to perform one or more functions in response to an immunogenic stimulus.

As used herein, "preventing the induction of" anergy in a T cell means fully or partially inhibiting the induction of anergy in the T cell.

As used herein, an "agonistic 4-1BB-binding agent" is a substance that upon binding to a 4-1BB molecule on a target cell (e.g., a T cell) enhances the response of the target cell to an immunogenic stimulus.

As used herein, a "functional fragment of a tumor-associated antigen (TAA)" is a fragment of a TAA shorter than the full-length TAA but with greater than 10% (e.g., greater than 10%, greater than 20%, greater than 30%, greater than 40%, greater than 50%, greater than 60%, greater than 70%, greater than 80%, greater than 90%, greater than 95%, greater than 98%, greater than 99%, greater than 99.5%, or 100% or more) of the ability of the full-length TAA to activate an immune response in the presence or absence of an agonistic 4-1BB-binding agent. In TAA that are polypeptides, a "full-length" TAA is the mature TAA, i.e. the polypeptide lacking its native signal sequence.

As used herein, a "peptide-epitope" of a polypeptide is a fragment of a polypeptide that binds to a major histocompatibility complex (MHC) molecule and is recognized in the form of a complex with the MHC molecule by an antigen specific receptor on a T cell (TCR). MHC molecules can be class I or class II MHC molecules.

"Polypeptide" and "protein" are used interchangeably and mean any peptide-linked chain of amino acids, regardless of length or post-translational modification.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., enhancing immune responses in mammalian subjects, will be apparent from the following description, from the drawings and from the claims.

DESCRIPTION OF DRAWINGS

FIGS. 3A and 3B are line graphs showing the cytolytic activity ("% Lysis") against the indicated target cells of effector cells at various effector target cell ratios ("E:T Ratio"). Mice were injected s.c. with either 1×10$^6$ C3 (FIG. 3A) or 4×10$^6$ EL4E7 (FIG. 3B) tumor cells on day 0. The mice were injected with 100 μg of either mAb 2A (open circles) or rat IgG (closed circles) on days 1 and 4. On day 7 the mice were sacrificed, tumor-draining lymph nodes (TDLN) were harvested, and the cells obtained from the TDLN were restimulated in vitro for four days with irradiated C3 cells (FIG. 3A) or irradiated EL4E7 cells (FIG. 3B). TDLN from 2-3 mice in each group were pooled. Cells harvested from the stimulating cultures were tested for cytolytic activity in a standard 4 hour $^{51}$Cr-release assay against EL4, EL4E7, RMA-S, E7 peptide-pulsed RMA-S ("RMA-S+E7"), or C3 target cells.

FIG. 15A is a series of line graphs showing the incidence of tumors in DBA/2 mice after immunization with either incomplete Freund's adjuvant alone ("IFA") or with IFA and a P1A peptide epitope ("P1A") and challenge with P815R tumor cells. On the day of immunization, and again three days later, P1A peptide-immunized mice were injected with either anti-CD137 mAb ("2A") or control rat IgG ("rat IgG"). All the mice were challenged with the P815R tumor cells 10 days after immunization and were observed for tumor incidence and regression at the indicated time points after tumor challenge ("Days after tumor inoculation").

FIG. 15B is a pair of line graphs showing the incidence of tumors in DBA/2 mice after immunization with IFA and a P1A peptide epitope and challenge with P815R tumor cells. The mice were immunized with IFA and the P1A peptide and were challenged with the P815R tumor cells 10 days after immunization. Three days after tumor challenge, and again three days later, the mice were injected with either anti-CD137 mAb ("2A") or control rat IgG ("rat IgG") and were observed for tumor incidence and regression at the indicated time points after tumor challenge ("Days after tumor inoculation").

DETAILED DESCRIPTION

Figure 1A:
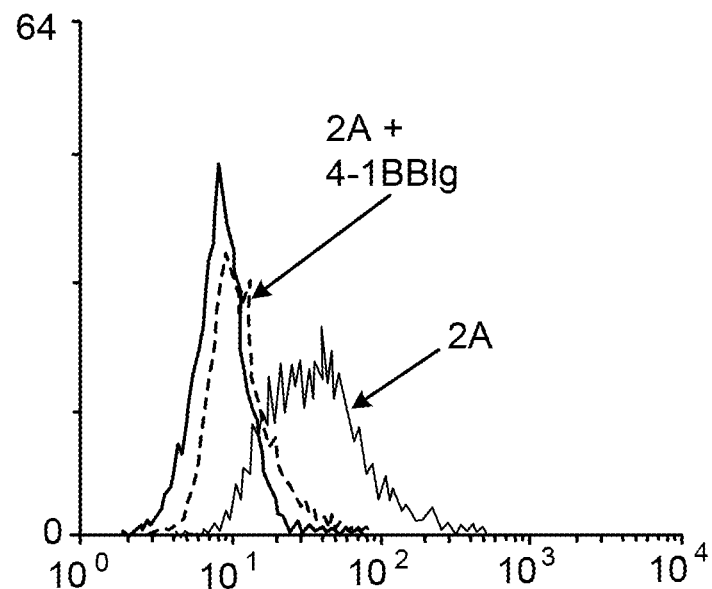
FIG. 1A is a flow cytometry (FFC) histogram showing the binding of mAb 2A (unfilled profile with solid line (labeled "2A") and unfilled profile with dashed line (labeled "2A+4-1BB")) or an isotype control antibody (filled profile) to nylon wool-purified murine T cells stimulated for 24 hours with immobilized antibodies specific for CD3 and CD28. The staining reactions were performed in the absence (unfilled profile with solid line and filled profile) or presence (unfilled profile with dashed line) of the murine 4-1BBIg fusion protein.

The invention is based on the finding that treatment of mice bearing a weakly immunogenic tumor with an agonistic antibody specific for murine 4-1BB and a peptide fragment of a polypeptide expressed by the tumor resulted in regression of the tumor. In addition, treatment of mice bearing a second weakly immunogenic tumor with the same 4-1BB antibody and autologous dendritic cells "primed" in vitro with cells of the tumor resulted in regression of the tumor. The inventors have also discovered that providing an immunogenic stimulus and a 4-1BB-mediated signal to a CD8+ T cell not only prevents induction of anergy in a CD8+ T cell, but can also reverse, partially or completely, already established anergy in a CD8+ T cell. These findings indicate that treatment of mammalian subjects having (or being at risk of having) cancer or an infectious disease with an agonistic agent that binds to the 4-1BB molecule (e.g., the 4-1BB ligand or an agonistic antibody specific for 4-1BB) and an immunogenic stimulus specific for the relevant cancer or infectious microorganism will result in an enhanced immune response to the cancer or infectious agent. Such an enhanced immune response will preferably, though not necessarily, be prophylactic and/or therapeutic for the relevant disease.

Methods of Activating an Immune Response

The invention features methods of activating mammalian immune responses in which cells of the immune system are exposed to (a) an immunogenic stimulus and (b) an agonistic 4-1BB-binding agent. Exposure of the cells to the immunogenic stimulus can occur before, during, or after exposure to the 4-1BB binding agent. The two exposures will preferably be substantially simultaneous.

Responses that are enhanced by the methods of the invention can be any immune response. The responses enhanced are preferably T cell responses. However, since antibody-producing responses of B cells are generally dependent on helper activity of activated CD4+ T cells, enhancement of a CD4+ T cell helper cell response can indirectly result in enhancement of a B cell antibody response. Similarly, the activities of other cells of the immune system (e.g., monocytes/macrophages, granulocytes (e.g., neutrophils), and natural killer cells) are regulated by T cells. Thus the methods of the invention can be used to enhance responses of any or all of these cell types.

The invention also provides methods for preventing induction of anergy in T cells or reversing anergy in T cells already rendered anergic. In these methods the relevant T cells are contacted with an immunogenic stimulus and a 4-1BB-binding agent. Contacting of the T cells with the immunogenic stimulus can occur before, during, or after contacting the T cells with the 4-1BB binding agent.

As used herein, an "immunogenic stimulus" is a stimulus delivered to a T cell via the antigen-specific T cell receptor (TCR) expressed on the surface of the T cell. More commonly, but not necessarily, such a stimulus is provided in the form of an antigen for which the TCR is specific. While such antigens will generally be protein, they can also be carbohydrates, lipids, nucleic acids or hybrid molecules having components of two or more of these molecule types, e.g., glycoproteins or lipoproteins. However, the immunogenic stimulus can also be provided by other agonistic TCR ligands such as antibodies specific for TCR components (e.g., TCR α-chain or β-chain variable regions) or antibodies specific for the TCR-associated CD3 complex. Immunogenic stimuli (as used herein) do not include antigen-non-specific stimuli provided by, for example, cytokines (e.g., interleukin-12), growth factors, co-stimulatory molecules, or adhesion molecules. While such stimuli can be exploited in the methods of the invention, they do not constitute the required immunogenic stimulus. Antigens useful as immunogenic stimuli include alloantigens (e.g., a MHC alloantigen) on, for example, an antigen presenting cell (APC) (e.g., a dendritic cell (DC), a macrophage, a monocyte, or a B cell). DC of interest are interdigitating DC and not follicular DC; follicular DC present antigen to B cells. For convenience, interdigitating DC are referred to herein as DC. Methods of isolating DC from tissues such as blood, bone marrow, spleen, or lymph node are known in the art, as are methods of generating them in vitro from precursor cells in such tissues. Also useful as immunogenic stimuli are polypeptide antigens and peptide-epitopes derived from them. Unprocessed polypeptides are processed by APC into peptide-epitopes that are presented to responsive T cells in the form of molecular complexes with MHC molecules on the surface of the APC. Useful immunogenic stimuli also include a source of antigen such as a lysate of either tumor cells or cells infected with an infectious microorganism of interest. APC (e.g., DC) pre-exposed (e.g., by coculturing) to antigenic polypeptides, peptide-epitopes of such polypeptides or lysates of tumor (or infected cells) can also be used as immunogenic stimuli. Such APC can also be "primed" with antigen by culture with a cancer cell or infected cell of interest; the cancer or infected cells can optionally be irradiated or heated (e.g., boiled) prior to the priming culture. In addition, APC (especially DC) can be "primed" with either total RNA, mRNA, or isolated TAA-encoding RNA.

Alternatively, antigen as an immunogenic stimulus be provided in the form of cells (e.g., tumor cells or infected cells producing the antigen of interest). In addition, immunogenic stimuli can be provided in the form of cell hybrids formed by fusing APC (e.g., DC) with tumor cells [Gong et al. (2000) Proc. Natl. Acad. Sci. USA 97(6):2716-2718; Gong et al. (1997) Nature Medicine 3(5):558-561; Gong et al. (2000) J. Immunol. 165(3):1705-1711] or infected cells of interest. Methods of fusing cells (e.g., by polyethylene glycol, viral fusogenic membrane glycoproteins, or electrofusion) are known in the art. In discussing these cell hybrids, the tumor or infected cell partners will be referred to as the immunogenic cells (IC). Cells or cell hybrids can be used (as immunogenic stimuli) untreated or they can be metabolically inhibited (e.g., by irradiation or exposure to a drug such as mitomycin-C) so as to substantially ablate their ability to divide. Tumor or infected cells used per se as an immunogenic stimulus or as IC for the production of cell hybrids will preferably, but not necessarily, be derived from the same donor as that of the T cell. Where the cells are from a different donor, they will preferably share one MHC haplotype with the T cell. APC used to form cell hybrids will also preferably, but not necessarily, be derived from the same donor as the T cell. In the production of cell hybrids, either the APC or the IC will be preferably be from, or MHC-compatible with, the donor of the T cell. Alternatively, the APC and/or the IC can share one MHC haplotype (i.e., be semi-allogeneic) with the donor of the T cell. However, as the cells or hybrids used as immunogenic stimuli will frequently be used in the presence of APC of the T cell donor (e.g., in in vivo applications), they can be fully MHC incompatible with the T cell.

Also useful as immunogenic stimuli are heat shock proteins bound to antigenic peptide-epitopes derived from antigens (e.g., tumor-associated antigens or antigens produced by infectious microorganisms) [Srivastava (2000) Nature Immunology 1(5):363-366]. Such complexes of heat shock protein and antigenic peptide are useful for facilitating or enhancing uptake of antigenic peptides by APC. Heat shock proteins of interest include, without limitation, glycoprotein 96 (gp96), heat shock protein (hsp) 90, hsp70, hsp 110, glucose-regulated protein 170 (grp 170) and calreticulin. Immunogenic stimuli can include one or more (e.g., one, two, three, four, five, six, seven, eight, nine, ten, more) heat shock proteins isolated from tumor cells or infected cells. Such tumor or infected cells are preferably, but not necessarily, from the same subject (i) whose immune response is to be enhanced by a method of the invention or (ii) from whom T cells (whose response is to be enhanced by a method of the invention) were obtained. The tumor or infected cells can also be obtained, for example, from another individual having the same or a related tumor-type or infection as the subject. Alternatively, the heat shock protein can be isolated from mammalian cells expressing a transcriptosome prepared from tumor cells or infected cells of interest.

Immunogenic stimuli can be derived from a wide range of infectious microorganisms (e.g., bacteria, fungi including yeasts, viruses, and parasites such as protozoan parasites). Examples of relevant microorganisms include, without limitation, *Mycobacteria tuberculosis, Salmonella enteriditis, Listeria monocytogenes, M. leprae, Staphylococcus aureus, Escherichia coli, Streptococcus pneumoniae, Borrelia burgdorferi, Actinobacillus pleuropneumonias, Helicobacter pylori, Neisseria meningitidis, Yersinia enterocolitica, Bordetella pertussis, Porphyromonas gingivalis*, mycoplasma, *Histoplasma capsulatum, Cryptococcus neoformans, Chlamydia trachomatis, Candida albicans, Plasmodium falciparum, Entamoeba histolytica, Toxoplasma brucei, Toxoplasma gondii, Leishmania major*; human immunodeficiency virus 1 and 2, influenza virus, measles virus, rabies virus, hepatitis virus A, B, and C, rotaviruses, papilloma virus, respiratory syncytial virus, feline immunodeficiency virus, feline leukemia virus, and simian immunodeficiency virus. Examples of relevant microbial proteins include, without limitation, the B subunit of heat labile enterotoxin of *E. coli* [Konieczny et al. (2000) FEMS Immunol. Med. Microbiol. 27(4):321-332], heat-shock proteins, e.g., the *Y. enterocolitica* heat shock protein 60 [Konieczny et al. (2000) supra; Mertz et al. (2000) J. Immunol. 164(3):1529-1537] and *M tuberculosis* heat-shock proteins hsp60 and hsp70, the *Chlamydia trachomatis* outer membrane protein [Ortiz et al. (2000) Infect. Immun. 68(3):1719-1723], the *B. burgdorferi* outer surface protein [Chen et al. (1999) Arthritis Rheum. 42(9):1813-1823], the *L. major* GP63 [White et al. (1999) Vaccine 17(17):2150-2161 (and published erratum in Vaccine 17(20-21):2755)], the *N. meningitidis* meningococcal serotype 15 PorB protein [Delvig et al. (1997) Clin. Immunol. Immunopathol. 85(2); 134-142], the *P. gingivalis* 381 fimbrial protein [Ogawa, (1994) J. Med. Microbiol. 41(5):349-358], the *E. coli* outer membrane protein F [Williams et al. (2000) Infect. Immun. 68(5):2535-2545], influenza virus hemagglutinins and neuramindases, retroviral (e.g., HIV) surface glycoproteins (e.g., HIV gp160/120), or retroviral tat or gag proteins. CTL are by virtue of their ability to kill target cells infected with any of a wide variety of intracellular pathogens (e.g., viruses, or intracellular bacteria and protozoans) potent mediators of immunity to such pathogens. Thus, since the methods of the invention are efficient at enhancing CTL responses, they can be used for prophylaxis and/or or therapy in infections with such intracellular pathogens. In addition, helper T cells release a wide variety of cytokines that mediate pathogen-destructive inflammatory responses.

As indicated above, immunogenic stimuli useful in the invention can be any of a wide variety of tumor cells, APC "primed" with tumor cells, hybrid cells (see above), tumor-associated antigens (TAA), peptide-epitopes of such TAA, and APC "primed" with TAA or peptide-epitopes of them. As used herein, a "TAA" is a molecule (e.g., a protein molecule) that is expressed by a tumor cell and either (a) differs qualitatively from its counterpart expressed in normal cells, or (b) is expressed at a higher level in tumor cells than in normal cells. Thus, a TAA can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart. Examples of relevant tumors that can be used per se or as a source of antigen (see above) include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, renal cell cancer, pancreatic cancer, genitourinary tumors such ovarian cancer, vaginal cancer, bladder cancer, testicular cancer, prostate cancer or penile cancer, bone tumors, and vascular tumors. Relevant TAA include, without limitation, carcinoembryonic antigen (CEA), prostate specific antigen (PSA), MAGE (melanoma antigen) 1-4, 6 and 12, MUC (mucin) (e.g., MUC-1, MUC-2, etc.), tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP) Bcl-2, and Ki-67. Both CTL and helper T cells have been shown to be efficient effectors of tumor immunity.

Where subjects are administered pathogenic agents (e.g., tumor cells, infectious microorganisms, or cells infected with infectious agents) in order to test for the efficacy of treatment with an agonistic 4-1BB-binding agent (optionally given with one or more non-specific agents such as cytokines (see above)), the pathogenic agents do not per se constitute an immunogenic stimulus for the purposes of the invention. Moreover, in a procedure that involves administration of an agonistic 4-1BB-binding agent (and optionally one or more non-specific agents such as cytokines (see above)) to a subject harboring pathogenic agents (e.g., tumor cells, infectious microorganisms, or cells infected with infectious agents) acquired by, for example, transformation of one or more cells in the subject or by natural infection, the harbored pathogenic agents do not per se constitute an immunogenic stimulus for the purposes of the invention.

The agonistic 4-1BB-binding agent can be an antibody specific for 4-1BB. As used herein, the term "antibody" refers not only to whole antibody molecules, but also to antigen-binding fragments, e.g., Fab, F(ab')$_2$, Fv, and single chain Fv fragments. Also included are chimeric antibodies. The antibody can be a polyclonal antibody or a monoclonal antibody (mAb)., e.g., the 2A mAb or the 5.9 and 5.10 mAbs described below. Alternatively, the agonistic 4-1BB-binding agent can be the natural 4-1BB ligand (4-1BBL) or a functional fragment of 4-1BB. As used herein, a functional fragment of 4-1BB means a fragment of 4-1BB that is shorter than full-length, mature 4-1BBL and has at least 10% (e.g., at least 10%, at least 20%, at least 30%, at least 40%, at least 50%, at least 60%, at least 70%, at least 80%, at least 90%, at least 95%, at least 98%, at least 99%, or 100% or more) of the ability of full-length mature 4-1BBL to enhance the response of a T cell to antigen of interest. Methods of testing and comparing the ability of molecules to enhance the response of T cells are known to investigators in the field, e.g., methods (or simple modifications of those) described in the Examples. While it is believed that 4-1BB-binding agents (e.g., antibodies) that bind to a domain of 4-1BB that is identical or overlapping with a domain to which 4-1BBL binds are not agonistic, the invention is not limited by any particular mechanism of action. Methods to test for agonistic activity in a candidate 4-1BB-binding agent would be essentially the same as those referred to above for testing the ability of a fragment of 4-1BBL for its ability to enhance the response of T cell to an immunogenic stimulus and thus well-known to those in the art.

The agonistic 4-1BB-binding agents can be added to the solution (e.g., blood or culture medium) containing the T cell. Alternatively, it can be secreted by or expressed on the surface of a cell in the vicinity of the T cell, e.g., an APC presenting an alloantigen or a peptide-epitope bound to an MHC molecule on the surface of the APC. Such cells can also be tumor cells, infected cells, or the cell hybrids described above. Where the agonistic 4-1 BB-binding agent is secreted by or bound to the surface of a cell, the cell can be, but is not necessarily, the same cell presenting an alloantigen or a peptide-epitope bound to an MHC molecule to the T cell. The methods of the invention require the provision of an exogenous source of the 4-1BB-binding agent. It is understood that where the agonistic 4-1BB-binding agent used in the methods of the invention is one secreted by or expressed on the surface of a cell such as an APC, tumor cell, infected cell, or hybrid cell, it will not be an agonistic 4-1BB-binding agent (e.g., 4-1BBL) naturally expressed by such cells. Where the only source of an agonistic 4-1BB-binding agent is that on the surface of or secreted by an APC, the agonistic 4-1BB-binding agent will be encoded by a recombinant 4-1BB encoding nucleic acid molecule in the APC. Moreover, fortuitous administration to a subject of an agonistic 4-1BB-binding agent present in, for example, blood, plasma, or serum administered to the subject for, e.g., therapeutic purposes, does not per se constitute administration of an agonistic 4-1BB-binding agent for the purposes of the invention. In addition, the fortuitous presence of an agonistic 4-1BB-binding agent in culture medium used for immune cell (e.g., T cell) activating cultures does not per se constitute the agonistic 4-1BB-binding agent required to be present in the in vitro methods of activating T cells of the invention.

If the activation is in vitro, the 4-1BB binding agent can be bound to the floor of a relevant culture vessel, e.g. a well of a plastic microtiter plate.

The agonistic 4-1BB-binding agent will preferably, but not necessarily, bind to 4-1BB on the surface of a T cell whose response is enhanced by the methods of the invention. However, 4-1BB is expressed on cells other than T cells, e.g., natural killer (NK) cells and monocytes [Melero et al. (1998) Cell. Immunol. 190:167-172; Kienzle et al. (2000) Int. Immunol. 12:73-82]. Thus, by binding to such non-T cells and thereby causing them to, for example, secrete helper cytokines or express on their surface costimulatory molecules and/or adhesion molecules, the response of the T cell or the response of a bystander cell (e.g., a B cell cell antibody response) that is "helped" by the T cell can be enhanced. Similarly, binding of a 4-1BB-binding agent to a CD4+ T cell can overcome anergy in a bystander CD4+ T cell or CD8+ T cell that is also exposed to an immunogenic stimulus by, for example, the action of cytokines produced by the CD4+ T cell to which the 4-1BB binding agent binds. In an analogous manner, binding of a 4-1BB-binding agent to a CD8+ T cell could overcome anergy in a bystander CD8+ T cell or CD4+ T cell exposed to an immunogenic stimulus.

Short amino acid sequences can act as signals to direct proteins (e.g., immunogenic stimuli or agonistic 4-1BB-binding agents) to specific intracellular compartments. For example, hydrophobic signal peptides (e.g., MAISGVPV-LGFFIIAVLMSAQESWA (SEQ ID NO:1)) are found at the amino terminus of proteins destined for the ER. While the sequence KFERQ (SEQ ID NO:2) (and other closely related sequences) is known to target intracellular polypeptides to lysosomes, other sequences (e.g., MDDQRDLISNNEQLP (SEQ ID NO:3) direct polypeptides to endosomes. In addition, the peptide sequence KDEL (SEQ ID NO:4) has been shown to act as a retention signal for the ER. Each of these signal peptides, or a combination thereof, can be used to traffic, for example the immunogenic stimuli or agonistic 4-1BB-binding agents to appropriate cellular compartments. Other signal sequences of interest include the $HIV_{tat}$ transduction domain (RKKRRQRR; SEQ ID NO:5), the Antennapedia homeodomain (RQIKIWFPNRRMKWKK; SEQ ID NO:6) and signal sequences derived from fibroblast growth factor [Lin et al. (1995) J. Biol. Chem. 220:14255-14258], transportan [Pooga et al. (1998) FASEB J. 12:67-77], and HSV-1 structural protein VP22 [Elliott et al. (1997) Cell 88:223-233]. Poly-arginine sequences (of 7 to 15 arginine residues) can also be used as membrane translocating domains. DNAs encoding the polypeptides containing targeting signals can be generated by PCR or other standard genetic engineering or synthetic techniques.

The immunogenic stimuli and agonistic 4-1BB-binding agents can have the amino acid sequences of naturally occurring molecules or they can have substitutions. Such substitutions will preferably be conservative substitutions. Conservative substitutions typically include substitutions within the following groups: glycine and alanine; valine, isoleucine, and leucine; aspartic acid and glutamic acid; asparagine, glutamine, serine, and threonine; lysine, histidine, and arginine; and phenylalanine and tyrosine.

Polypeptides useful for the invention also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptide compounds can be covalently or noncovalently coupled to pharmaceutically acceptable "carrier" proteins prior to administration.

Also of interest are peptidomimetic compounds that are designed based upon the amino acid sequences of polypeptides of interest. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to activate an immune response (in the case of immunogenic stimuli) and enhance an immune response (in the case of the agonistic 4-1BB-binding agents). Peptidomimetic compounds can have additional characteristics that enhance their in vivo utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Molecules useful as immunogenic stimuli and agonistic 4-1BB-binding agents can be produced by any of a wide range of methods known in the art. They can be purified from natural sources (e.g., from any of the pathogenic agents listed herein). Smaller peptides (fewer than 100 amino acids long) and other non-protein molecules can be conveniently synthesized by standard chemical means known to those in the art. In addition, both polypeptides and peptides can be manufactured by standard in vitro recombinant DNA techniques and in vivo transgenesis using nucleotide sequences encoding the appropriate polypeptides or peptides (see Nucleic Acids section below). Methods well-known to those skilled in the art can be used to construct expression vectors containing relevant coding sequences and appropriate transcriptional/translational regulatory elements. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

The transcriptional/translational regulatory elements referred to above include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

The expression systems that may be used for purposes of the invention include but are not limited to microorganisms such as bacteria (for example, *E. coli* and *B. subtilis*) transformed with recombinant bacteriophage DNA, plasmid DNA, or cosmid DNA expression vectors containing a nucleic acid molecules encoding immunogenic stimuli or agonistic 4-1BB-binding agents; yeast (for example, *Saccharomyces* and *Pichia*) transformed with recombinant yeast expression vectors containing a nucleic acid encoding immunogenic stimuli or agonistic 4-1BB-binding agents; insect cell systems infected with recombinant virus expression vectors (for example, baculovirus) containing a nucleic acid encoding immunogenic stimuli or agonistic 4-1BB-binding agents; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing a nucleotide sequence encoding immunogenic stimuli or agonistic 4-1BB-binding agents; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

Cells transfected or transduced with the expression vectors of the invention can then be used, for example, for large or small scale in vitro manufacture of an immunogenic stimulus or agonistic 4-1BB-binding agent by methods known in the art. In essence, such methods involve culturing the cells under conditions that maximize production of the polypeptide and isolating the polypeptide from the cells or from the culture medium.

For the methods of the invention, it is often required that the immunogenic stimuli and/or agonistic 4-1BB-binding agents be purified. Methods for purifying biological macromolecules (e.g., proteins) are known in the art. The degree of purity of the macromolecules can be measured by any appropriate method, e.g., column chromatography, polyacrylamide gel electrophoresis, or HPLC analysis.

A T cell whose response is enhanced, whose anergy is reversed, or in which induction of anergy is prevented by the methods of the invention can be a CD4+ T cell or a CD8+ T cell. The invention is not limited by: (a) the T cell having any particular phenotype (e.g., CD4+ or CD8+) or function (e.g., cytotoxicity, helper activity, immune deviating activity, or suppressive activity); or (b) the MHC molecules by which the T cell is restricted being of any particular class. While the majority of T cells with cytotoxic activity are CD8+ and recognize peptide-epitopes bound to MHC class I molecules, CD4+ CTL that recognize antigenic peptides bound to MHC class II molecules are known in the art. CD4+ CTL that recognize peptides bound to MHC class I molecules and CD8+ CTL that recognize antigenic peptides bound to MHC class II molecules have also been described. In addition, while the majority of T cells with helper and/or immune deviating activity are CD4+ T cells and recognize antigenic peptides bound to MHC class II molecules, these activities have also been observed in MHC class I restricted CD8+ T cells. Similarly, while most immunosuppressive T cells are CD8+ T cells, CD4+ T cells with immunosuppressive activity have also been demonstrated. The methods of the invention are applicable to all these T cells. Preferred responses will be those of MHC class I restricted CTL and MHC class II restricted CD4+ helper/immune deviating T cells. Responses of MHC class I restricted CTL are particularly preferred.

The methods of the invention can be performed in vitro or in vivo.

In Vitro Methods

In vitro applications can be useful, for example, in basic scientific studies of immune mechanisms or for production of activated T cells for use in either studies on T cell function or, for example, passive immunotherapy. Furthermore, a 4-1BB-binding agent can be added to in vitro assays (e.g., in T cell proliferation assays) designed to test for immunity to an antigen of interest in a subject from which the T cells were obtained. Addition of a 4-1BB-binding agent to such assays would be expected to result in a more potent, and therefore more readily detectable, in vitro response. However, the methods of the invention will preferably be in vivo or ex vivo (see below).

In the in vitro methods of the invention, lymphoid cells (consisting of or including T cells) obtained from a mammalian subject are cultured with any of the above described immunogenic stimuli and agonistic 4-1BB-binding agents. The lymphoid cells can be from a subject pre-exposed to a relevant antigen (in any of the forms described above); alternatively, the donor of the lymphoid cells need not have been exposed to the antigen. The cultures can also be supplemented with one or more cytokines or growth factors such as, without limitation, interleukin-(IL-)1, IL-2, IL-3, IL-4, IL-6, IL-7, IL-12, IL-13, IL-15, interferon-γ (IFN-γ), tumor necrosis factor-α (TNF-α), granulocyte macrophage colony-stimulating factor (GM-CSF), or granulocyte-colony stimulating factor (G-CSF). The cultures can be "restimulated" as often as necessary. The cultures can also be monitored at various times to ascertain whether the desired level of immune reactivity (e.g., CTL or helper T cell activity) has been attained.

In Vivo Methods

The methods of the invention are generally useful for enhancing immune responses, reversing anergy in T cells, or preventing the induction of anergy in T cells. Immune responses generated can be prophylactic or therapeutic. However, the responses generated need have neither prophylactic nor therapeutic efficacy. They can be used, for example, (a) to produce large numbers of activated T cells for use in basic scientific studies of T cell activity; or (b) to enhance T cell responses that provide helper activity for antibody-producing B cells and thereby facilitate the production of large quantities of antibodies in mammals (e.g., rabbits, goats, sheep, or horses) that are subsequently isolated from the animals and used for purposes such as antigen detection or purification, or (c) for immunization of animals (e.g., mice, rats, or hamsters) with a view to making monoclonal antibodies.

The methods of the invention can be used, for example, for prophylaxis or therapy against (a) infectious diseases due to any of the infectious agents listed herein; or (b) cancers such as any of those listed herein. In addition to being useful for the treatment of a wide variety of cases, in cases where a subject is at relatively high risk for a cancer (e.g., prostate cancer in men over 50 years of age, lung cancer in a tobacco smoker, or melanoma in a subject with multiple nevi), appropriate methods can be used for prophylaxis. In regard to infectious microorganisms, the methods can be particularly useful in the prevention and/or therapy of diseases involving intracellular microorganisms (i.e. infectious agents that replicate inside a cell), e.g., viruses such as influenza virus or HIV, intracellular bacteria such *M tuberculosis*, and intracellular protozoans such as *P. falciparum* or any of the other infectious agents listed herein.

As used herein, "prophylaxis" can mean complete prevention of the symptoms of a disease, a delay in onset of the symptoms of a disease, or a lessening in the severity of subsequently developed disease symptoms. "Prevention" of a disease should mean that symptoms of the disease (e.g., an infection) are essentially absent. As used herein, "therapy" can mean a complete abolishment of the symptoms of a disease or a decrease in the severity of the symptoms of the disease. As used herein, a "protective" immune response is an immune response that is prophylactic and/or therapeutic.

The methods of the invention can be applied to a wide range of species, e.g., humans, non-human primates (e.g., monkeys), horses, cattle, pigs, sheep, goats, dogs, cats, rabbits, guinea pigs, hamsters, rats, and mice. The immunogenic stimuli and agonistic 4-1BB-binding agents can be derived from any of these species. They will preferably be, but not necessarily, used to generate immune responses of cells of the species from which they were derived.

In one in vivo approach, one or more of any of the above the immunogenic stimuli and one or more of any of the above the agonistic 4-1BB-binding agents (in any of the forms described above) are administered to a subject of any of the above mammalian species. The immunogenic stimuli can be administered at the same time as the agonistic 4-1BB-binding agent(s), or separately, i.e., before or after administration of the agonistic 4-1BB-binding agent(s). Generally, the immunogenic stimuli and the agonistic 4-1BB-binding agents, whethered administered per se or administered in the form of recombinant cells either secreting them or expressing them on their surfaces, will be suspended in a pharmaceutically-acceptable carrier (e.g., physiological saline) and administered orally or transdermally or injected (or infused) intravenously, subcutaneously, intramuscularly, intraperitoneally, intrarectally, intravaginally, intranasally, intragastrically, intratracheally, or intrapulmonarily. They can be delivered directly to an appropriate lymphoid tissue (e.g. spleen, lymph node, or mucosal-associated lymphoid tissue (MALT)). The dosage required depends on the route of administration, the nature of the formulation, the nature of the patient's illness, the subject's size, weight, surface area, age, and sex, other drugs being administered, and the judgment of the attending physician. Suitable dosages for soluble immunogenic stimuli and soluble agonistic 4-1BB-binding agents are in the range of 0.01-100.0 mg/kg. Wide variations in the needed dosage are to be expected in view of the variety of immunogenic stimuli and agonistic 4-1BB-binding agents available and the differing efficiencies of various routes of administration. For example, oral administration would be expected to require higher dosages than administration by intravenous injection. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the immunogenic stimuli and/or agonistic 4-BB-binding agents in a suitable delivery vehicle (e.g., polymeric microparticles or implantable devices) may increase the efficiency of delivery, particularly for oral delivery. In addition, adjuvants can be used together with the immunogenic stimuli. Suitable adjuvants include cholera toxin (CT), *E. coli* heat labile toxin (LT), mutant CT (MCT) [Yamamoto et al. (1997) J. Exp. Med. 185:1203-1210] and mutant *E. coli* heat labile toxin (MLT) (Di Tommaso et al. (1996) Infect. Immunity 64:974-979]. MCT and MLT contain point mutations that substantially diminish toxicity without substantially compromising adjuvant activity relative to that of the parent molecules. Other useful adjuvants include alum, Freund's complete and incomplete adjuvant, and RIBI. In addition, one or more of the above-listed cytokines or growth factors can be administered (by any of the routes recited herein) to the subject, before, at the same time as, or after administration of immunogenic stimuli or agonistic 4-1BB-binding agents. Moreover, where tumor cells, APC, or hybrid cells are used as the immunogenic stimulus, such cells, in addition to expressing on their surface or secreting recombinant agonistic 4-1BB-binding agents, can also express on their surface or secrete either (a) one or more recombinant costimulatory molecules (e.g., B7.1, B7.2, B7-H1, B7-H2, B7-H3, or B7-H4) and/or (b) one or more recombinant cytokines or recombinant growth factors such as those listed above, e.g., GM-CSF. Cells expressing on their surface or secreting the above recombinant molecules will have been transfected (stably or transiently) or transformed with one or more nucleic acids (e.g., expression vectors) encoding the molecules.

Alternatively, one or more polynucleotides containing nucleic acid sequences encoding one or more immunogenic stimuli and/or one or more agonistic 4-1 BB-binding agents of interest can be delivered to an appropriate cell of the animal. Expression of the coding sequences will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotides are encapsulated in these microparticles, which are taken up by macrophages and gradually biodegraded within the cell, thereby releasing the polynucleotide. Once released, the nucleic acid sequence are expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 µm and preferably larger than 20 µm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73, 479]. Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), Mol. Cell. Biol. 12, 1043-1053; Todd et al. (1993), J. Exp. Med. 177, 1663-1674; Penix et al. (1993), J. Exp. Med. 178, 1483-1496]. Delivery of "naked DNA" (i.e., without a delivery vehicle) to an intramuscular, intradermal, or subcutaneous site is another means to achieve in vivo expression.

In the relevant polynucleotides (e.g., expression vectors) the nucleic acid sequence encoding the relevant immunogenic stimulus (or agonistic 4-1BB-binding agent) with an initiator methionine and optionally a targeting sequence (see above), is operatively linked to a promoter or enhancer-promoter combination.

A promoter is a TRE composed of a region of a DNA molecule, typically within 100 basepairs upstream of the point at which transcription starts. Enhancers provide expression specificity in terms of time, location, and level. Unlike a promoter, an enhancer can function when located at variable distances from the transcription site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles which are suitable for administration to a human or other mammalian subject, e.g., physiological saline. A therapeutically effective amount is an amount of the polynucleotide that is capable of producing a medically desirable result (e.g., a detectable T cell response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes and frequency of administration can be any of those listed above.

Ex Vivo Methods

In one ex vivo approach, lymphoid cells, including T cells (CD4+ and/or CD8+ T cells), are isolated from a subject and exposed to one or more immunogenic stimuli and one or more agonistic 4-1BB-binding agents in vitro (see above). Such T cells can be, for example, anergic T cells in which it is desired to reverse anergy. The lymphoid cells can be exposed once or multiply (e.g., 2, 3, 4, 6, 8, or 10 times). The level of immune activity (e.g., CTL activity) in the lymphoid cells can be tested after one or more exposures. Once the desired activity and level of that activity is attained, the cells are reintroduced into the subject (or another subject) via any of the routes listed herein. The therapeutic or prophylactic efficacy of this ex vivo approach is dependent on the ability of the ex vivo activated lymphocytes to exert, directly or indirectly, a neutralizing or cytotoxic effect on, for example, infectious microorganisms, host cells infected with microorganisms, or tumor cells.

An alternative ex vivo strategy can involve transfecting or transducing cells obtained from a subject with one or more polynucleotides encoding one or more immunogenic stimuli and one or more agonistic 4-1BB-binding agents. The transfected or transduced cells are then returned to the subject or another subject. While such cells would preferably be hemopoietic cells (e.g., bone marrow cells, macrophages, monocytes, dendritic cells, or B cells) they could also be any of a wide range of types including, without limitation, fibroblasts, epithelial cells, endothelial cells, keratinocytes, or muscle cells in which they act as a source of the one or more immunogenic stimuli and one or more agonistic 4-1BB-binding agents for as long as they survive in the subject. The use of hemopoietic cells, that include the above APC, would be particularly advantageous in that such cells would be expected to home to, among others, lymphoid tissue (e.g., lymph nodes or spleen) and thus the immunogenic stimuli and agonistic 4-1BB-binding agents would be produced in high concentration at the site where they exert their effect, i.e., enhancement of an immune response. In addition, if APC expressing a transgene encoding one or more agonistic 4-1BB-binding agents are used, the APC expressing the exogenous can be, but are not necessarily, the same APC that presents an alloantigen or antigenic peptide to the relevant T cell. The agonistic 4-1BB-binding agents can be secreted by the APC or expressed on its surface. Prior to administering recombinant APC to a subject, they can optionally be exposed to the above-listed sources of antigens or antigenic peptides of interest, e.g., those of tumors or infectious microorganisms. The same genetic constructs and trafficking sequences described for the in vivo approach can be used for this ex vivo strategy. Furthermore, tumor cells or hybrid cells produced by fusion of APC (e.g., dendritic cells) and tumor cells can be transfected or transformed by one or more vectors encoding one or more agonistic 4-1BB-binding agents. Such cells, preferably treated with an agent (e.g., ionizing irradiation or mitomycin C) that ablates their proliferative capacity, are then administered to a subject with the relevant cancer where, due to their expression of the exogenous agonistic 4-1BB-binding agents (on their cell surface or by secretion), they can stimulate enhanced tumoricidal T cell immune responses. It is understood that the tumor cells which, after transfection or transformation with agonistic 4-1BB-binding agent encoding nucleic acids, are administered to a subject with cancer can have been obtained from an individual other than the subject. Similarly, tumor cells used for the production of hybrid cells that express recombinant agonistic 4-1 BB-binding agents and are administered to a subject with cancer, can have been obtained from an individual other than the subject.

The ex vivo methods can include the steps of harvesting cells (e.g., tumor cells or APC) from a subject, culturing the cells, transducing them with one or more expression vectors, and maintaining the cells under conditions suitable for expression of the immunogenic stimuli and/or agonistic 4-1BB-binding agents. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the coding sequence or of a drug resistance gene. The cells may then be lethally irradiated (if desired) and injected or implanted into the patient. The methods can include the additional step of making the above-described cells hybrids that are injected or implanted into the patient.

It is understood that the methods of invention can involve combinations of the above in vivo and ex vivo approaches. Thus, for example, an immunogenic stimulus can be provided in the form of a peptide-epitope and agonistic 4-1BB-binding agent in the form of either a nucleic acid encoding it or cells transformed with a nucleic acid encoding it.

The methods of the invention can be applied to any of the diseases and species listed here. Methods to test whether a given modality is therapeutic for or prophylactic against a particular disease are known in the art. Where a therapeutic effect is being tested, a test population displaying symptoms of the disease (e.g., cancer patients) is treated by a method of the invention, using any of the above described strategies. A control population, also displaying symptoms of the disease, is treated, using the same methodology, with a placebo. Disappearance or a decrease of the disease symptoms in the test subjects would indicate that the method was therapeutic.

By applying the same strategies to subjects prior to onset of disease symptoms (e.g., presymptomatic subjects considered to likely candidates for cancer development (see above) or experimental animals in which an appropriate disease spontaneously arises or can be deliberately induced, e.g., multiple murine cancers, the method can be tested for prophylactic efficacy. In this situation, prevention of onset of disease symptoms is tested. Analogous strategies can be used to test for the efficacy of the methods in the prophylaxis of a wide variety of infectious diseases, e.g., those involving any of the microorganisms listed above.

4-1BB-Specific Antibodies

The invention features antibodies that bind specifically to human and mouse 4-1BB. Such antibodies can be polyclonal antibodies present in the serum or plasma of animals (e.g., mice, rabbits, rats, guinea pigs, sheep, horses, goats, cows, or pigs) that have been immunized with the relevant 4-1BB polypeptide (or a peptide fragment thereof) using methods, and optionally adjuvants, known in the art. Such polyclonal antibodies can be isolated from, for example, serum, plasma, or ascites by methods known in the art. Monoclonal antibodies (mAb) that bind to 4-1BB polypeptides or fragments are also encompassed by the invention. These mAbs include those produced by the 2A, 5.9, and 5.10 hybridomas (see Examples). Methods of making and screening monoclonal antibodies are well known in the art. Once the desired antibody-producing hybridoma has been selected and cloned, the resulting antibody can be produced by a number of in vivo and in vitro methods known in the art. For example, the hybridoma can be cultured in vitro in a suitable medium for a suitable length of time, followed by the recovery of the desired antibody from the supernatant. The length of time and medium are known or can be readily determined.

Additionally, recombinant antibodies specific for 4-1BB, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240:1041-43; Liu et al. (1987) J. Immunol. 139:3521-26; Sun et al. (1987) PNAS 84:214-18; Nishimura et al. (1987) Canc. Res. 47:999-1005; Wood et al. (1985) Nature 314:446-49; Shaw et al. (1988) J. Natl. Cancer Inst. 80:1553-59; Morrison, (1985) Science 229:1202-07; Oi et al. (1986) BioTechniques 4:214; Winter, U.S. Pat. No. 5,225,539; Jones et al. (1986) Nature 321:552-25; Veroeyan et al. (1988) Science 239:1534; and Beidler et al. (1988) J. Immunol. 141:4053-60.

Also included within the scope of the invention are antibody fragments and derivatives which contain at least the functional portion of the antigen binding domain of an antibody that binds specifically to 4-1BB. Antibody fragments that contain the binding domain of the molecule can be generated by known techniques. For example, such fragments include, but are not limited to: $F(ab')_2$ fragments that can be produced by pepsin digestion of antibody molecules; Fab fragments that can be generated by reducing the disulfide bridges of $F(ab')_2$ fragments; and Fab fragments that can be generated by treating antibody molecules with papain and a reducing agent. See, e.g., National Institutes of Health, 1 Current Protocols In Immunology, Coligan et al., ed. 2.8, 2.10 (Wiley Interscience, 1991). Antibody fragments also include Fv (e.g., single chain Fv (scFv)) fragments, i.e., antibody products in which there are few or no constant region amino acid residues. An scFv fragment is a single polypeptide chain that includes both the heavy and light chain variable regions of the antibody from which the ScFv is derived. Such fragments can be produced, for example, as described in U.S. Pat. No. 4,642,334, which is incorporated herein by reference in its entirety.

The following Examples are meant to illustrate, not limit, the invention.

EXAMPLES

Example 1

Materials and Methods

Tumor Models and Peptides C3 cells, generated from HPV-16-/EJras-transformed C57BL/6 (B6) mouse embryo cells [Feltkamp et al. (1993) Eur. J. Immunol. 23:2242-2249], were a gift from Dr. W. Martin Kast (Loyola University, Chicago, Ill.). A line of EL4 cells (EL4E7) transfected with cDNA encoding the human papilloma virus-16 (HPV-16) E7 polypeptide [Tindle et al. (1995) Clin. Exp. Immunol. 101: 265-271] was a gift from Dr. Germain J. P. Fernando (University of Queensland, Brisbane, Australia). The TC-1 cell line [Liu et al. (1996) Cancer Res. 56:21-6] was a gift from Dr. T. C. Wu (Johns Hopkins University, Baltimore, Md.) and the B16-F10 melanoma line [Dranoff et al. (1993) Proc. Natl. Acad. Sci. USA 90:3539-3543] was a gift from Dr. Glenn Dranoff (Dana-Farber Cancer Institute, Boston, Mass.). The EL4, RMA-S and S49.1 murine T cell lymphoma lives were of B6 origin and were purchased from the American Type Culture Collection (Manassas, Va.). The regressor P815 mastocytoma (P815R), which has been previously described [Nieland et al. (1999) J. Cell Biochem 73:145-152], was obtained from Dr. W. Martin Kast, Loyola University, Chicago, Ill. All cell lines were maintained in a complete tissue culture medium of RPMI 1640 (Life Technologies, Carlsbad, Calif.) supplemented with 10% fetal bovine serum (FBS) (HyClone, Logan, Utah), 25 mM HEPES, 2 mM glutamine, 100 U/ml penicillin G and 100 µg/ml streptomycin sulfate.

The E7 peptide (RAHYNIVTF) (SEQ ID NO:7) contained the minimal H-2$D^b$-restricted CTL epitope [Feltkamp et al. (1993) Eur. J. Immunol. 23:2242-2249] of HPV-16 E7 protein. The trp-2 peptide (SVYDFFVWL) (SEQ ID NO:8) is a H-2$K^b$-restricted epitope first identified in the B16 melanoma [Bloom et al. (1997) J. Exp. Med. 185:453-459; Schreurs et al. (2000) Cancer Res. 60:6995-7001]. The Vp2 control peptide (FHAGSLLVFM) (SEQ ID NO:9) contains an H-2$D^b$-restricted CTL epitope derived from the Theiler's Murine Encephalomyelitis Virus [Johnson et al. (1999). J. Virol. 73:3702-3708]. The OVA (257-264) peptide (SIINFEKL) (SEQ ID NO:10) (referred to in the OT-1 T cell anergy experiments described in Examples 10-13 as the "OVA peptide") is a H-2$K^b$-restricted CTL epitope derived from chicken ovalbumin [Curtsinger et al. (1998) J. Immunol. 160:3236-3243; Moore et al. (1988) Cell 54:777-785]. The OVA (55-62) peptide (KVVRFDKL) (SEQ ID NO: 11) used as a "control peptide" in the OT-1 T cell anergy experiments described in Examples 10-13 is a H-2$K^b$-restricted CTL epitope from chicken ovalbumin [El-Shami et al. (1999) Eur. J. Immunol. 29:3295-3301] The P1A (35-43) peptide (LPYLGWLVF) (SEQ ID NO:12) is an H-2$L^d$ restricted CTL epitope. All peptides were synthesized by the Mayo Molecular Biology Core Facility and the purity of the peptides was >90% by reverse-phase HPLC purification. The peptides were dissolved in dimethyl sulfoxide (DMSO) and reconstituted in phosphate buffered saline (PBS) to a final concentration of 1 mg/ml (5% DMSO) for administration to mice.

Female B6 mice were purchased from the National Cancer Institute (Frederick, Md.). Age-matched mice, 6-10 weeks old, were used for all experiments. Tumor cells in 0.1 ml of PBS were injected subcutaneously (s.c.) into the right shaved flanks. Mice were given $1 \times 10^6$ C3 cells or $4 \times 10^6$ EL4E7 cells. Tumor size (the average of two perpendicular diameters in mm) was measured weekly as previously described [Tamada et al. (2000) Nature Med. 6:283-289]. For lung metastases models, $1 \times 10^4$ TC-1 or $1 \times 10^5$ B16-F10 cells were injected in 0.5 ml of Hank's Buffered Salt Solution into the tail vein of mice. Mice bearing subcutaneous tumors were immunized intradermally (i.d.) at a site contralateral to the tumor with 50 µg of peptide emulsified in incomplete Freund's adjuvant (IFA) (Sigma Chemicals, St. Louis, Mo.). Mice bearing lung metastases were immunized bilaterally i.d. with a total of 100 pg of peptide emulsified in IFA. Antibodies administered to mice were injected intraperitoneally (i.p.) in 0.5 ml of PBS.

For experiments involving challenge with P815R tumor cells, $1.5 \times 10^4$ P815R cells were injected intradermally into the shaved flanks of DBA/2 mice.

OT-1 transgenic mice, which have been previously described [Strome et al. (2002) Cancer Research 62:1884-1889], were obtained from Dr. Larry Pease, Mayo Clinic, Rochester, Minn. All the CD8+ T cells of the OT-1 mice express an antigen specific T cell receptor (TCR) specific for the OVA (257-264) peptide bound to the murine H-2$K^b$ MHC class 1 molecule.

Antibodies, Tetramers, and Fusion Protein To prepare a 4-1BBIg fusion protein, cDNA encoding the extracellular domain of mouse 4-1BB was amplified from cDNA produced from RNA isolated from concanavilin A-activated spleen cells using sequence specific primers and was fused to the $CH_2$—$CH_3$ domain of mouse IgG2a in the expression plasmid pmIgV [Chapoval et al. (2000) Nature Med. 6:283-289]. The resulting expression vector was transfected into CHO cells. The protein in the culture supernatants of a transfected clone was purified using a HiTrap Protein G-Sepharose column (Amersham Pharmacia Biotech, Piscataway, N.J.) and dialyzed into lipopolysaccharide-free PBS.

A rat monoclonal antibody (mAb) against 4-1BB was generated by immunizing a Lewis rat (Harlan Sprague Dawley, Indianapolis, Ind.) with mouse 4-1BBIg. Hybridomas were produced by fusing rat spleen cells with mouse Sp2/0 myeloma cells and the culture supernatants were screened by ELISA. The hybridoma secreting the mAb 2A was selected for further experiments. Hybridoma 2A was grown in RPMI 1640 supplemented with 10% low IgG FBS (Life Technologies) and 25 mM HEPES and supernatant was harvested and concentrated using a tangential flow miniplate concentrator (Millipore, Bedford, Mass.). The 2A mAb was purified from the concentrated supernatant using a 5 ml HiTrap Protein G-Sepharose column (Amersham Pharmacia Biotech, Piscataway, N.J.). The purified mAb was dialyzed against PBS and concentrated using a Centriprep concentrator (Millipore, Bedford, Mass.). The isotype of the 2A mAb was determined using biotinylated, isotype-specific antibodies (Caltag Laboratories, Burlingame, Calif.). It was found to be an IgG2a antibody with kappa light chains.

Purified mAb specific for mouse CD3, CD28, 4-1BB, fluorescein isothiocyanate-(FITC-) conjugated CD8, CD69, CD25, CD49A, and isotype control mAb, and Cy-Chrome-conjugated CD8 mAb were purchased from PharMingen (San Diego, Calif.). The FITC-conjugated goat anti-rat IgG antibody was purchased from Biosource International (Camarillo, Calif.). Rat IgG antibodies (Sigma Chemical, Gilbertsville, Pa.) were used as controls.

Tetramers of the mouse H-2$D^b$ major histocompatibility complex (MHC) class I molecule bound to either the E7 peptide (H-2$D^b$-E7) or the control Vp2 peptide (H-2$D^b$-Vp2) were prepared as previously described [Johnson et al. (1999) J. Virol. 73:3702-3708]. Briefly, H-2$D^b$ α-chain and human $β_2$-microglobulin were isolated from a bacterial expression system and subsequently folded in the presence of excess peptide. The folded monomeric complexes were desalted and biotinylated. Following cation exchange purification, the monomeric complexes were conjugated to strepavidin labeled with the fluorescent dye, phycoerythin (PE), thereby forming fluorescent tetrameric complexes. The PE-labeled tetramers generated were then purified by size exclusion gel filtration.

A tetramer composed of four mouse H-2$K^b$ molecules bound to the OVA (257-264) peptide and labeled with PE (sometimes referred to below as the "OVA tetramer") was obtained from the NIH tetramer core facility (Atlanta, Ga.).

T Cell Costimulation Assay The method used to assay costimulatory activity of mAb was described previously [Tamada et al. (2000) Nature Med. 6:283-289]. Briefly, nylon wool (NW)-purified mouse splenic T cells ($2.5 \times 10^6$/ml) were added to 96-well plates which had been coated with a mAb against CD3 (0.1 µg/ml) and the indicated concentrations of rat IgG or mAb 2A. The proliferation of T cells was assessed by the addition of 1 µCi/well of [$^3$H]-thymidine ($^3$H-TdR) to the 3-day cultures 15 hours before harvesting of the cultures onto fiber glasstilters. $^3$H-TdR incorporated into the T cells was measured in a MicroBeta TriLux liquid scintillation counter (Wallac, Turku, Finland).

FACS Analysis and Sorting T cells were positively selected using FITC conjugated mAbs against CD4 and CD8, metal microbeads coated with antibody specific for FITC, and a magnet as instructed by the manufacturer (Miltenyi Biotec, Auburn, Calif.). The purity of the isolated T cells was routinely greater than 95%, as assessed by flow cytometry using a mAb against CD3. Purified T cells ($2.5 \times 10^6$ cells/ml) from mouse spleens were stimulated in the wells of 24-well tissue culture plates coated with mAbs against CD3 (5 μg/ml) and CD28 (1 μg/ml). After 24 hours, T cells were collected and stained for 30 min at 4° C. with 1 μg mAb 2A, either alone or in the presence of 4-1BBIg (2 μg/ml), in 50 μl PBS supplemented with 3% FBS and 0.02% azide. The cells were washed and incubated an additional 30 min at 4° C. with FITC-conjugated goat antibody specific for rat IgG. After washing the cells were fixed in 1% paraformaldehyde and fluorescence was analyzed with a FACS (Becton Dickinson, Mountain View, Calif.). S49.1 cells were stained in a similar fashion. In brief, $1 \times 10^6$ S49.1 cells were stained with either mAb 2A or the mAb specific for 4-1BB purchased from Pharmingen (clone 1AH2). After washing, the cells were stained with a FITC-conjugated antibody specific for rat IgG, washed, fixed and analyzed.

Tumor-draining lymph nodes (TDLN) from immunized mice were harvested on day 7 and stained with PE-labeled H-2D$^b$E7 or H-2D$^b$-Vp2 tetrameric complexes and FITC-conjugated CD8 as previously described [Johnson et al. (1999) J. Virol. 73:3702-3708]. Five×$10^6$ TDLN cells were incubated with $2.5 \times 10^5$ UV-irradiated C3 cells for 4 days. Cells were subsequently stained with the PE-labeled tetramers and FITC-conjugated CD8. After extensive washing, cells were re-suspended in PBS with 750 ng/ml propidium iodide. Gates were drawn to include viable CD8+ cells only.

FACS analysis for the OT-1 T cell anergy experiments was performed essentially as described above but using the staining reagents indicated below.

For FACS sorting of OT-1 TCR expressing T cells, T cells were purified from spleens and lymph nodes of mice using microbead coated with antibody specific for Thy1.2 according to the manufacturers instructions (Miltenyi Biotec, San Diego, Calif.). Purified Thy1.2+ cells were subsequently stained with the OVA tetramer described above. Positively stained cells were sorted using a FACSVantage Flow Cytometry System (B D Immunocytometry Systems, San Jose, Calif.). At least 90% of the sorted cells were both OVA tetramer positive and CD8+.

Assay for CTL Activity In the experiments on the C3 tumor, effector cells were obtained by co-culturing draining LN cells with irradiated C3 cells for 4 days. Effector cells were harvested from the cultures and tested for CTL activity using a standard 4-hr $^{51}$Cr release assay with tumor cell targets at the indicated effector to target cell (E:T) ratios. Peptide-pulsed target cells were generated by culturing the target cells with 10 μg/ml of the peptide at 28° C. for 18 hours prior to use. The CTL assay used for the OT-1 T cell anergy experiments was performed similarly using the target cells indicated below.

Preparation of Murine DC Murine DC were prepared from bone marrow. Mice were sacrificed and dipped in 70% ethanol (EtOH). After removing excess EtOH, the hind limbs were exposed and the hip joint dislocated. Muscle parenchyma was removed and the bones placed briefly in 70% EtOH and then in complete medium (CM; RPMI 1640, 10% heat inactivated FBS (Hyclone Laboratories, Inc., Logan, Utah), Fungizone (0.5 μg/ml), n-ME ($2 \times 10^{-5}$M), sodium pyruvate (1 mM), non-essential amino acids (0.1 mM), penicillin and streptomycin (100 μg/ml), glutamine (2 mM) and Gentamycin (50 μg/ml)). Both ends of the bones were cut to expose the marrow and a 3 cc syringe (filled with CM) with a 25 gauge needle was used to eject the marrow into a 10 mm cell culture dish, containing CM. Following marrow extraction, the cells were separated from stromal components by straining through a steel sieve and, after pelleting by centrifugation, were resuspended in 1.0 ml medium of containing 10 μg/ml of anti-class II (I-A$^b$) mAb, anti-Mac 3 mAb, anti-CD8a mAb (HO2.2), anti-CD45R (B220) mAb, anti-CD3e mAb, and anti-GR-1 mAb (all from PharMingen, Inc. San Diego, Calif.), and incubated on ice for 20 minutes. The cells were then washed once and resuspended in rabbit serum (diluted 1:30 in medium) (Cedarlane Laboratories, Ltd., Hornby, Ontario, Canada) as a source of lytic complement at a concentration of $10^7$ cells/ml and incubated at 37° C. for 45 minutes. The cells were then washed, plated in 100 mm cell culture dishes at a concentration of $10^7$ cells in 10 ml of CM supplemented with 10 ng/ml granulocyte macrophage-colony stimulating factor (GM-CSF) and 1 ng/ml interleukin-4 (IL-4), and cultured at 37° C. Non-adherent cells were removed from the cultures on day 2 and discarded and the cultures containing highly purified DC were harvested on day 5.

Induction of T Cell Anergy $3-7 \times 10^6$ lymph node and spleen cells from OT-1 mice were injected intravenously (i.v.; tail vein) into wild type B6 mice in 0.5 ml Hanks balanced salt solution (HBSS) (Cellgro, Herndon, Va.). 12-24 hours later, experimental mice were given 0.5 mg of OVA (257-264) peptide i.v. in 0.5 ml total volume, while control mice were given OVA (55-62) peptide (or PBS alone in some experiments) in a similar fashion. On the day of peptide administration, and again 3 days later, mice were given 100 μg of either rat IgG or anti-CD137 mAb intraperitoneally (i.p.). Mice were sacrificed at various time points following peptide administration and the total number of OT-1 cells present in the spleen and lymph nodes of each mouse was determined by OVA tetramer staining. For restimulation experiments, ten days following the administration of peptide, spleens were harvested from the mice. After lysing red blood cells in Ack lysis buffer, the spleen cells were resuspended in RPMI tissue culture medium supplemented as described above for the medium used to culture tumo cell lines and plated in triplicate into the wells of a 96-well plate at a density of $5.5 \times 10^5$ cells per well in final volume of 200 μl per well. One group of cells was unstimulated while a second group was restimulated with 1 ng/ml of OVA peptide. The same day that splenocytes were restimulated, the frequency of OVA-specific T cells was determined using the H-2K$^2$-OVA (257-264) tetramer. Thus, the absolute number of OT-1 cells added to each well could be calculated prior to restimulation in vitro. Supernatants were collected from the wells in each group 48 and 72 hours after restimulation and IL-2 (48 hr) and IFN-γ (72 hr) production was measured by sandwich ELISA following the manufacturer's instructions (PharMingen, San Diego, Calif.). The proliferation of T cells was assessed by the addition of 1 μCi/well [$^3$H]-thymidine during the last 15 hours of the 3-day culture. [$^3$H]-thymidine incorporation was measured in a MicroBeta TriLux liquid scintillation counter (Wallac, Turku, Finland). Antigen specific proliferation or cytokine production per OT-1 cell was calculated by subtracting any nonspecific proliferation (or cytokine production) observed in the unstimulated groups from the proliferation (or cytokine production) observed in the peptide stimulated groups. This was then divided by the number of OT-1 cells ($10^3$) initially present in the well prior to restimulation to derive the net change in cpm (Δcpm) per $10^3$ OT-1 cells.

To measure the ability of anti-CD137 to reverse anergy, OT-1 cells were adoptively transferred into wild type recipients. Anergy was induced by the intravenous administration of 0.5 mg OVA peptide as described above. Alternatively, mice received only control peptide or PBS and were considered "naïve" at the time of rechallenge with the antigen. Ten days later mice were given 0.5 mg OVA peptide or control peptide intravenously. Mice received 100 μg of either rat IgG or anti-CD137. Mice were sacrificed at various time points following rechallenge with the OVA peptide and the number of OT-1 cells present in the spleen and lymph nodes of each mouse was determined by tetramer analysis, as before.

Example 2

Figure 1B:
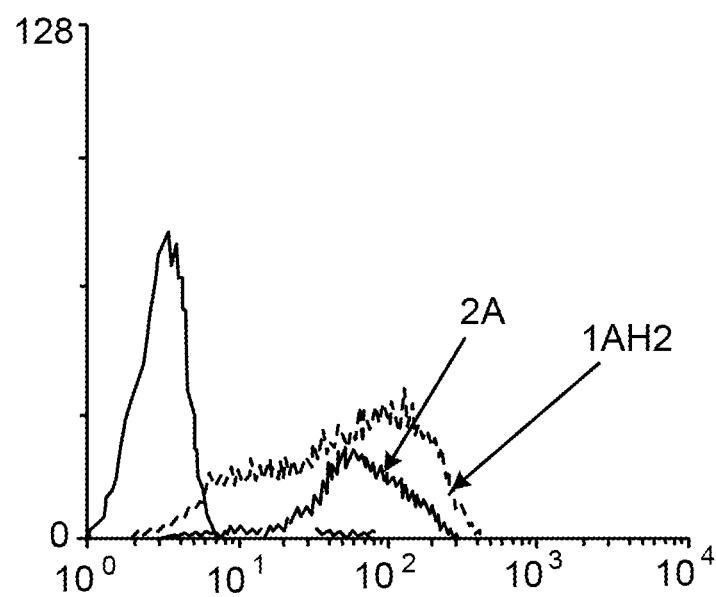
FIG. 1B is a FFC histogram showing binding of mAb 2A (unfilled profile (labeled "2A")), a commercially available mAb specific for murine 4-1 BB (unfilled profile labeled "1AH2"), or an isotype control antibody (filled profile) to S49.1 murine T lymphoma cells.
Figure 1C:
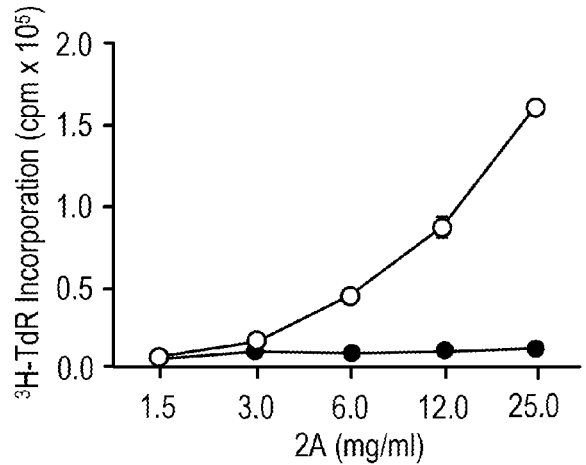
FIG. 1C is a line graph showing the proliferation ("$^3$H-TdR Incorporation") in counts per minute ("cpm×10$^5$") of nylon wool-purified murine T cells stimulated with antibody specific for mouse CD3 (coated onto well-bottoms of 96-well tissue culture plates at a concentration of 0.1 μg/ml) and either mAb 2A (open circles) or rat IgG (filled circles), each coated onto the well-bottoms of the 96-well tissue culture plates at the indicated concentrations.

The Anti-4-1BB mAb 2A and its In Vivo Antitumor Effect on EL4E7 Lymphoma and C3 Epithelioma The specificity of anti-4-1BB mAb was examined. Monoclonal antibody 2A stained >80% of purified T cells that had been activated for 24 hours by anti-CD3 and anti-CD28 mAbs. Binding of the antibody was specific as it could be competitively inhibited by inclusion of mouse 4-1BBIg in the staining reaction (FIG. 1A) while inclusion of a control rat IgG antibody did not inhibit binding (data not shown). Furthermore, mAb 2A binds specifically to the mouse T cell lymphoma 549.1 that constitutively expresses 4-1BB (as demonstrated by staining with 1AH2, a commercially available anti-4-1BB mAb (FIG. 1B)). Immobilized mAb 2A also enhanced T cell proliferation in a dose-dependent fashion in the presence of a suboptimal dose of anti-CD3 mAb (FIG. 1C). Therefore, 2A is a costimulatory mAb similar to others previously described [Melero et al. (1997) Nature Med. 3:682-685; Shuford et al. (1997) 186:47-55].

Figure 2:
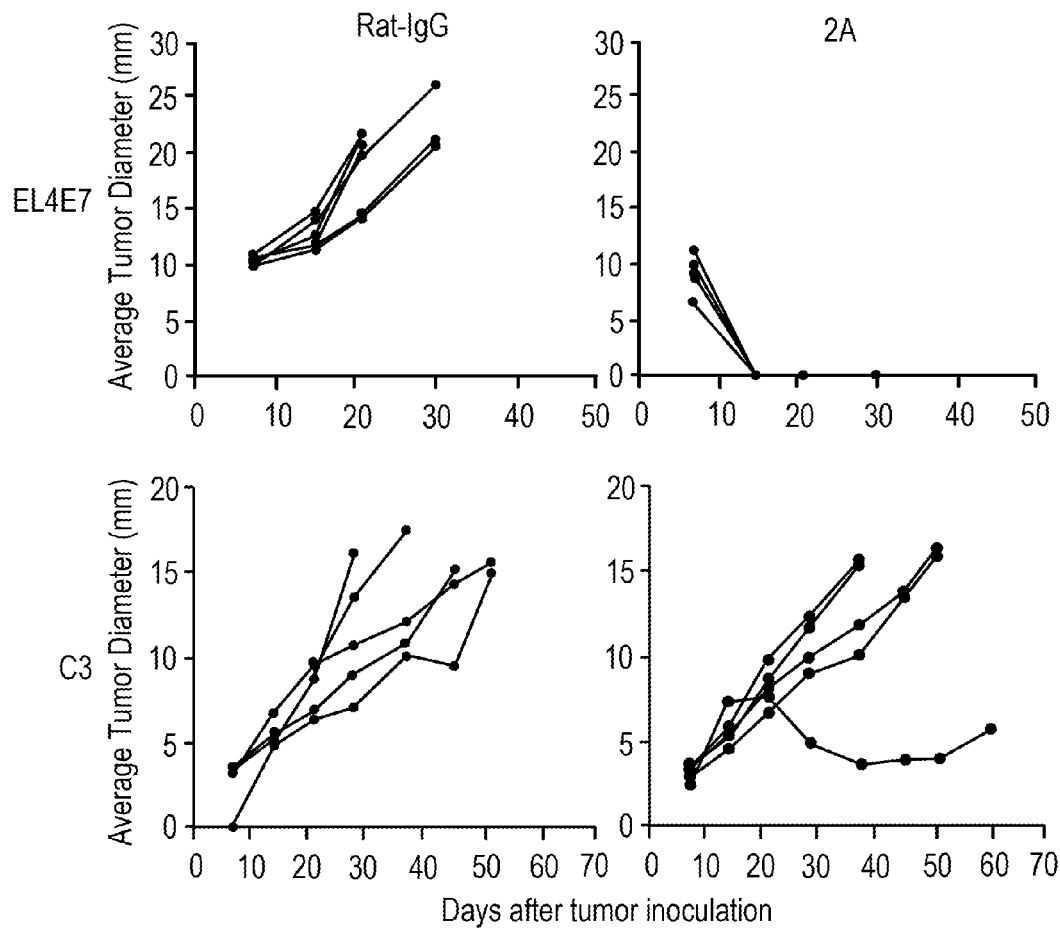
FIG. 2 is a series of line graphs showing the growth ("Average Tumor Diameter") of tumors in mice injected subcutaneously (s.c.) with C3 tumor cells (bottom panels) or EL4E7 tumor cells (top panels) on day 0, Seven days after injection of the tumor cells the mice were injected with either mAb 2A (right panels) or rat IgG (left panels). Each line represents a single mouse.

To test whether mAb 2A induces the regression of established tumors, two mouse tumors were selected. EL4E7 is a thymoma transfected to express the HPV-16 E7 gene and C3 is an embryonic epithelial cell line transformed with HPV-16 and the ras oncogene. Since both tumor lines express the E7 gene of HPV-16, CTL responses to the E7 gene product can be monitored. To determine the antitumor effect of mAb 2A, groups of mice bearing established EL4E7 or C3 tumors were injected i.p. with 2A (100 μg) at days 7 and 10. As shown in FIG. 2, established EL4E7 tumors regressed rapidly in the mice injected with 2A while tumors grew progressively in the mice treated with a control rat IgG antibody (FIG. 2). Remarkably, EL4E7 tumors up to 12 mm in diameter regressed within 7 days following treatment. In sharp contrast, treatment of mice bearing C3 tumors less than 4 mm in diameter had only a marginal effect. As shown in a representative experiment (FIG. 2), retardation of tumor growth occurred in one out of five mice; tumors in the other four mice grew progressively. The results indicate that, although anti-4-1BB mAb eradicates established EL4E7 tumors, C3 tumors are refractory to treatment. This resistance to treatment is unlikely due to the size of the tumor or to any antigenic disparity between the tumors.

Example 3

Presence of CTL that are Ignorant of the E7 Antigens in C3-Bearing Mice is Associated with Resistance to mAb 2A Treatment To understand the mechanisms underlying the resistance of C3 tumors to 2A mAb treatment, the activation status of tumor-specific CTL in mice bearing C3 tumors was examined. Mice were first inoculated subcutaneously (s.c.) with C3 cells and subsequently (3-7 days later) treated with mAb 2A or control rat IgG. Seven days later, TDLN were harvested, re-stimulated in vitro with irradiated C3 cells, and the CTL activity of cells harvested from cultures was tested in a standard $^{51}$Cr release assay. As shown in FIG. 3A, neither EL4E7 nor C3 were lysed by the in vitro activated TDLN in C3-bearing mice, even if the mice from which the TDLN were obtained had been treated with mAb 2A. It is unlikely that the failure to detect CTL activity was due to insensitivity of the assay as CTL activity could not be detected against RMA-S cells pulsed with the E7 peptide or EL4E7 cells, both of which are highly sensitive target cells. In sharp contrast, E7-specific CTL activity is routinely detected in TDLN isolated from EL4E7-bearing mice; in addition, this E7-specific CTL activity is enhanced by treatment with 2A mAb (FIG. 3B). What would appear to be non-specific lysis of the wild type RMA-S cells in this assay may be explained by the recent observation that EL4 and RMA-S cells share a tumor antigen [Van Hall et al. (2000) J. Immunol. 165:869-877].

Figure 4A:
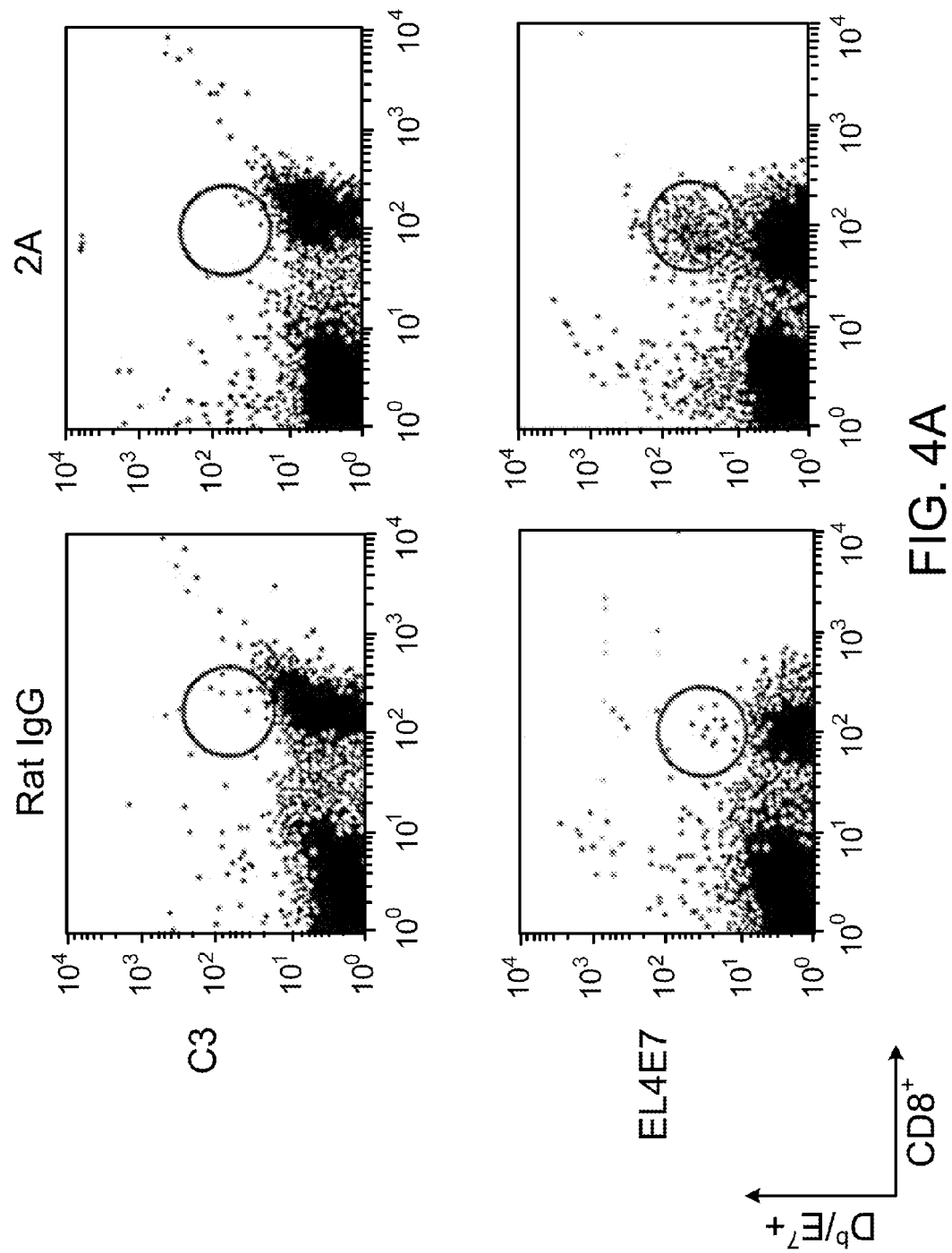
FIG. 4A is a series of two-dimensional FFC histograms showing the binding to cells (obtained from cultures set up as described for FIG. 3) of mAb specific for CD8 and tetramers of H-2D$^b$ class molecules bound to the E7 (49-57) peptide ("D$^b$/E7"). Data obtained with cells from mice injected with C3 cells are shown in the top two panels and data obtained with cells from mice injected with EL4E7 cells are shown in the bottom two panels. The mice were injected with either the 2A mAb (left panels) or rat IgG (right panels). The circles within the histograms indicate the area gated to detect cells binding both the CD8-specific mAb and the D$^b$/E7 tetramer.
Figure 4B:
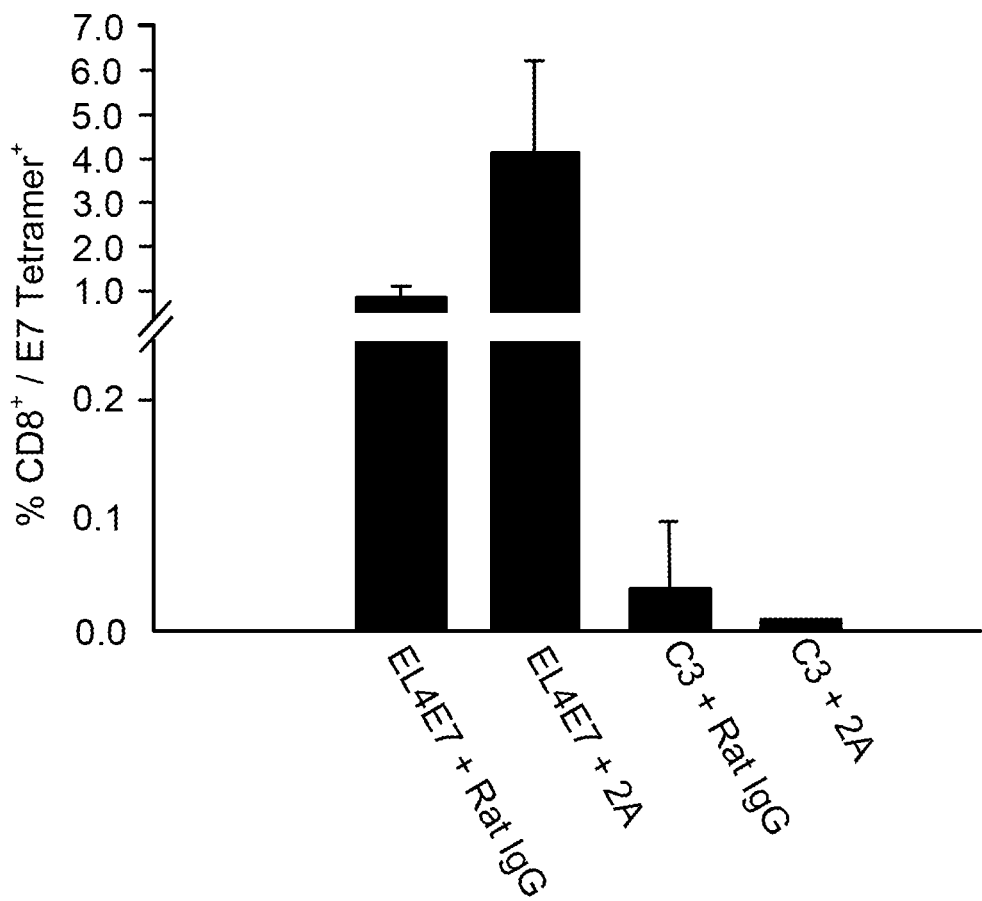
FIG. 4B is a bar graph showing the relative number of cells (in the cell populations described in FIG. 4A) binding both the CD8-specific mAb and the D$^b$/E7 tetramer ("% CD8$^+$/E7 Tetramer$^+$"). Thus, the cells were from cultures set up from mice injected with: C3 cells and rat IgG ("C3+Rat IgG": top left histogram in FIG. 4A); C3 cells and mAb 2A ("C3+2A"; top right histogram in FIG. 4A); EL4E7 cells and rat IgG ("EL4E7+Rat IgG"; bottom left histogram in FIG. 4A); and EL4E7 cells and mAb 2A ("EL4E7+2A"; bottom right histogram in FIG. 4A).

The frequency of E7 (49-57) specific T cells in C3 TDLN was determined by double staining with FITC conjugated anti-CD8 mAb and PE-labeled E7 tetramer. Consistent with the findings on CTL activity, less than 0.1% of $CD8^+$ T cells in TDLN from C3-bearing mice were E7-specific, even after in vitro re-stimulation with irradiated C3 cells. This value represents a threshold of "undetected CTL" in the assay since similar results were also obtained using cells from naïve mice. Furthermore, treatment with the 2A mAb failed to expand E7-specific CTL in C3 TDLN (FIG. 4A, B). In contrast, ~1% of $CD8^+$ cells were E7-specific in the draining LN of EL4E7-bearing mice treated with the control antibody after restimulation with irradiated C3 cells. Treatment with mAb 2A in vivo promoted the expansion of E7-specific CTL, as demonstrated by a 4-fold increase in the frequency of E7-specific T cells (FIG. 4B). The frequency of E7-specific CTL thus to correlated with CTL activity. More importantly, the results indicate that the absence of active E7 specific CTL, rather than suppressed cytolytic activity of specific CTL, in TDLN of C3 bearing mice is responsible for the inability of 2A mAb to boost T cell responses.

Figure 5A:
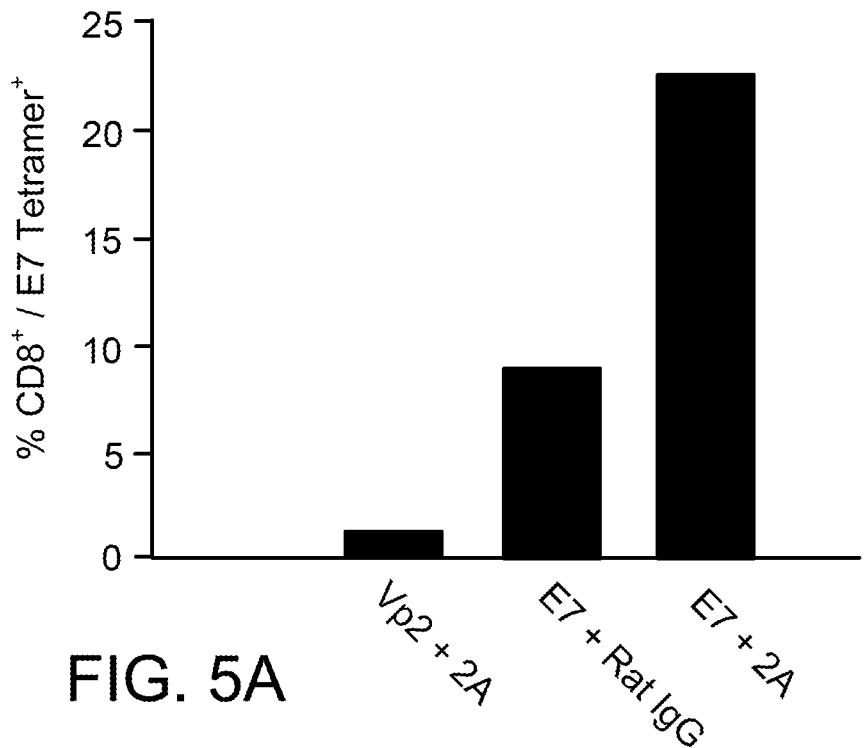
FIGS. 5A and 5B are bar graphs showing the relative number of cells binding both the CD8-specific mAb and the $D^b$/E7 tetramer ("% CD8$^+$/E7 Tetramer$^+$") in lymph nodes from mice treated as follows. Normal mice (FIG. 5B) or mice injected s.c. (in one flank) seven days earlier with $1\times10^3$ C3 cells (FIG. 5A) were immunized by s.c. injection in the contralateral flank with 50 μg of the E7 (49-57) peptide (or the control Vp2 peptide) emulsified in incomplete Freund's adjuvant (IFA). The mice injected with the Vp2 peptide and some of the mice injected with the E7 (49-57) peptide were injected i.p. with 100 μg of mAb 2A ("Vp2+2A" and "E7+2A", respectively) on the day following, and four days after, immunization. Other mice injected with the E7 (49-57) peptide were injected i.p. with 100 pg of rat IgG ("E7+Rat IgG") on the day following, and four days after, immunization. Seven days after immunization with peptide the mice were sacrificed and lymph nodes draining the site of immunization were removed. Lymph nodes from 2-3 mice per group were pooled. Cell suspensions were prepared from the lymph nodes and the relative number of cells binding both CD8 and the $D^b$/E7 tetramer ("% CD8$^+$/E7 Tetramer$^+$") were determined as described above for FIG. 4.
Figure 5B:
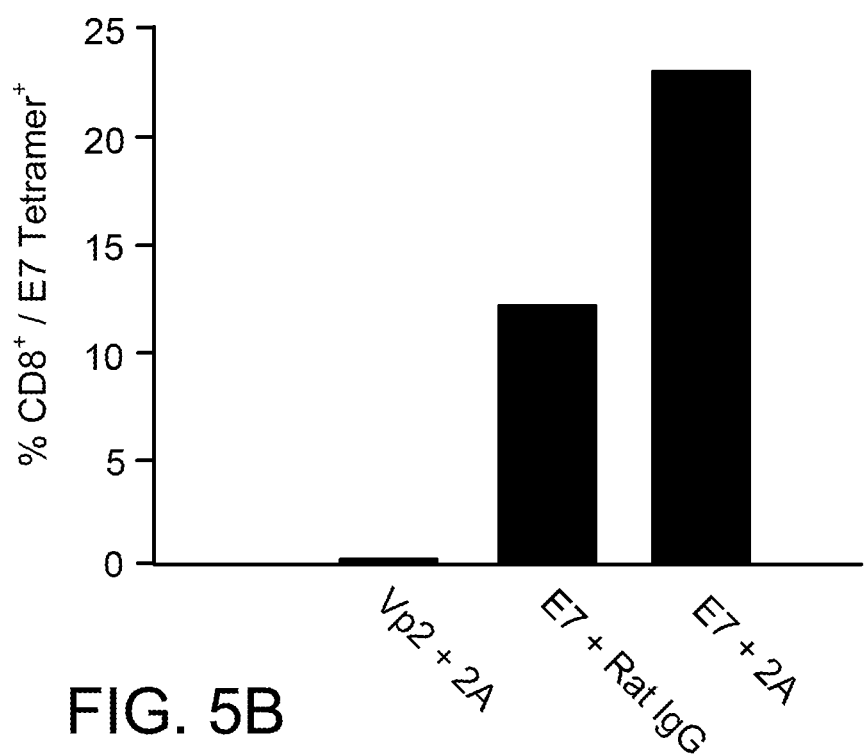

To exclude the possibility that E7-specific CTL are deleted in C3-bearing mice, E7-specific CTL activity was examined in the mice after immunization with the E7 (49-57) peptide that contains a H-2D$^b$ restricted CTL epitope. Seven days after peptide immunization, draining LN were harvested, restimulated with irradiated C3 cells and the frequency of E7 specific $CD8^+$ T cells was determined using the fluorescent E7 tetramer. Immunization with the E7 peptide caused a significant increase of cells that bound the E7 tetramer. Such cells were not detectable after immunization with a control Vp2 peptide. Treatment with mAb 2A resulted in a further increase in the frequency of E7-specific CTL (FIG. 5A). Similar results were obtained by immunization of naïve mice (FIG. 5B). Therefore, E7-specific CTL are present in C3-bearing mice, but are neither activated nor deleted by the C3 cells. Thus ET-specific CTL ignore antigens presented by the C3 tumor. In addition, anti-4-1BB mAb alone is unable to break this ignorant state.

Example 4

Figure 6:
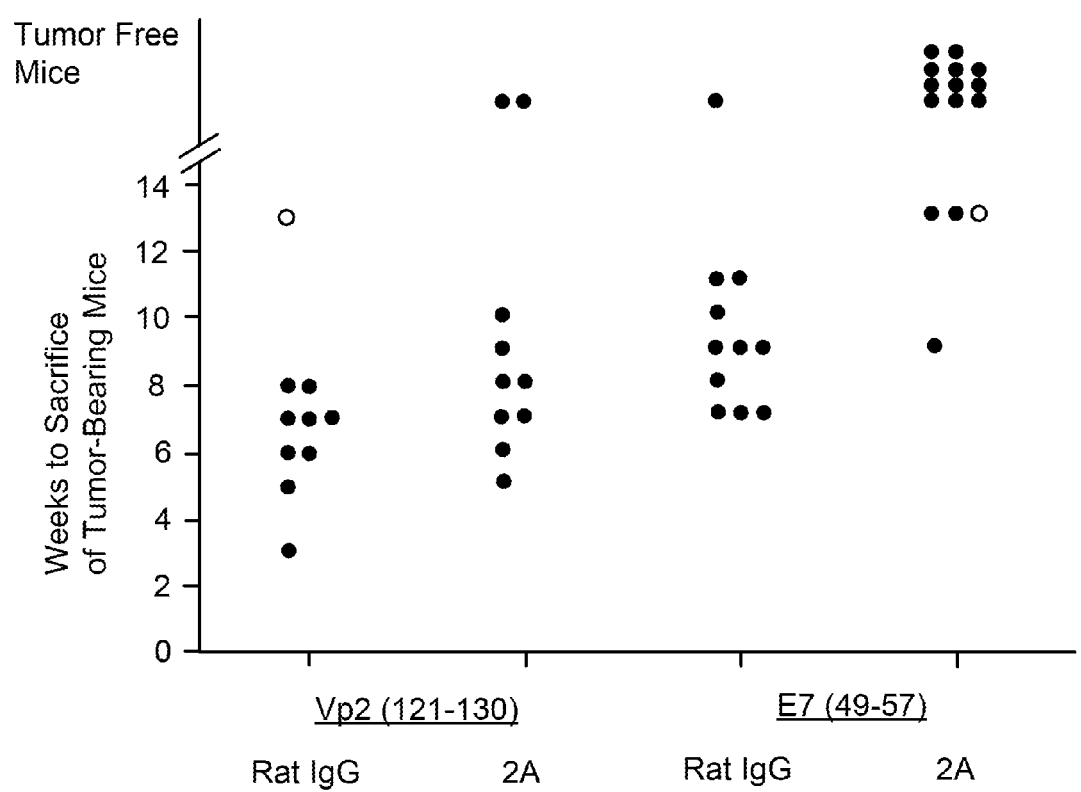
FIG. 6 is a scattergram showing (in mice treated as described below) (i) the number of mice that never developed palpable tumors and (ii) the number of weeks after injection of tumor cells that had elapsed when the indicated mice were sacrificed, i.e., when the tumors in the mice attained an average diameter of 15 mm. The mice were treated as follows. All mice were injected s.c. with $1\times10^6$ C3 cells on day 0. On day 7, half the mice were immunized s.c. with the E7 (49-57) peptide and the other half with the control Vp2 (121-130) peptide emulsified in IFA. On days 7 and 10, the mice were injected i.p. with either 100 μg of mAb 2A ("2A") or rat IgG ("Rat IgG"). Tumor size was assessed weekly for each mouse and the mice were sacrificed when the average tumor diameter reached 15 mm (open circles). Mice bearing tumors less than 15 mm in average tumor diameter at the termination of the experiment (week 13) are indicated by open circles. Mice that never developed palpable tumors are indicated by closed circles in the top part of the figure.

Regression of Established C3 Epithelioma by Breaking CTL Ignorance with E7 Epitope Peptide and Anti-4-1BB mAb 2A As shown in Example 3, immunization with the E7 epitope peptide increases CTL frequency in C3-bearing mice. An experiment was designed to test whether immunization with the E7 peptide is an effective treatment for established C3 tumors. Mice bearing C3 tumors for 7 days were immunized with either E7 or the control Vp2 peptide and the mice were observed for at least 12 weeks following treatment. They were sacrificed after the tumor reached 15 mm in diameter. Tumor regression was observed in only 1 of 11 (9%) mice treated with the E7 peptide only. Therefore, E7 peptide immunization is not sufficient to treat established C3 tumors. However, tumors completely regressed in 11 of 15 (73%) mice that had received a combined treatment with costimulatory 4-1BB mAb plus E7 peptide (COPP). In addition, those tumors that failed to regress in mice after COPP treatment grew more slowly when compared to tumors in the control groups (FIG. 6). Only 2 of 10 (20%) control mice treated with mAb 2A and the control Vp2 peptide were tumor free. The mice treated with the control Vp2 peptide and rat IgG antibody reached 15 mm in diameter within 8 weeks, with the exception of a single mouse bearing a smaller tumor (<15 mm) for more than 12 weeks (FIG. 6). Therefore, COPP treatment effectively induced the regression of established C3 tumors.

Whether COPP treatment is also effective in treating larger C3 tumors was determined. As summarized in Table 1, mice bearing C3 tumors for 14 days (5-8 mm in diameter at the time of treatment) were treated with COPP. Tumor regression was observed in 16 of 38 (42%) mice. In contrast, tumor regression was observed in 0%, 9% and 0%, respectively, in mice treated with E7 peptide, mAb 2A alone or the control Ig and Vp2 peptide. Tumors that failed to completely regress in the mice given COPP treatment were also significantly smaller 21 days following treatment than tumors observed in all three control groups of mice.

TABLE 1

Treatment of mice bearing large C3 tumors.

| Treatment[a] | | | | |
| --- | --- | --- | --- | --- |
| Antibody | Peptide | Tumor Free/Total (%) | Mean Tumor Diameter (mm)[b] | P-value[c] |
| 2A | E7(49-57) | 16/38 (42%) | 7.6 +/− 2.4 | — |
| Control Ig | E7(49-57) | 0/11 (0%) | 10.5 +/− 3.0 | 0.017 |
| 2A | Vp2(121-130) | 2/23 (9%) | 11.4 +/− 4.0 | 0.004 |
| Control Ig | Vp2(121-130) | 0/8 (0%) | 11.5 +/− 3.5 | 0.005 |

[a]Mice were injected with $1 \times 10^6$ C3 cells. Two weeks later, mice were immunized with the indicated peptide. On the day of immunization and 3 days later, mice were given 100 µg of mAb 2A or a control rat IgG i.p. Tumor size was assessed weekly. Data shown was pooled from several experiments.
[b]21 days following treatment, the mean tumor diameter was calculated for those tumors which had failed to completely regress.
[c]The Unpaired Student's T-test was used to calculate p-values comparing the mean tumor diameter of the treatment group which received both the E7 peptide and mAb 2A with those of the control groups.

Example 5

Figure 7A:
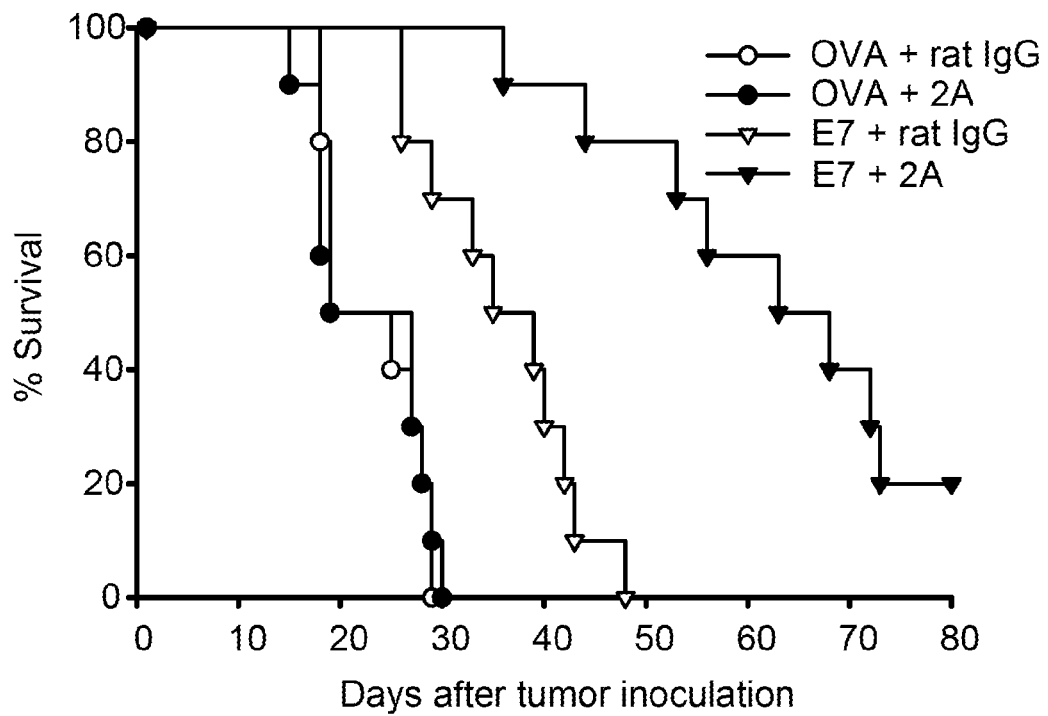
FIGS. 7A and 7B are survival curves showing the survival ("% Survival") of mice treated as follows. Mice were injected intravenously (i.v.) with either $1\times10^6$ TC-1 cells (FIG. 7A) or $1\times10^5$ B16-F10 cells on day 0. On day 3, the mice were injected s.c. with either the control OVA peptide or (circles), the E7 (49-57) ("E7") peptide (triangles in FIG. 7A), or the trp-2 peptide (triangles in FIG. 7B) (50 μg of the indicate peptide emulsified in IFA in each flank). On day 3 and on day 6 the mice were injected with 100 μg of either the 2A mAb ("2A") or rat IgG. The mice were observed daily for the duration of the experiment. Survival data from two identically performed experiments were combined.
Figure 7B:
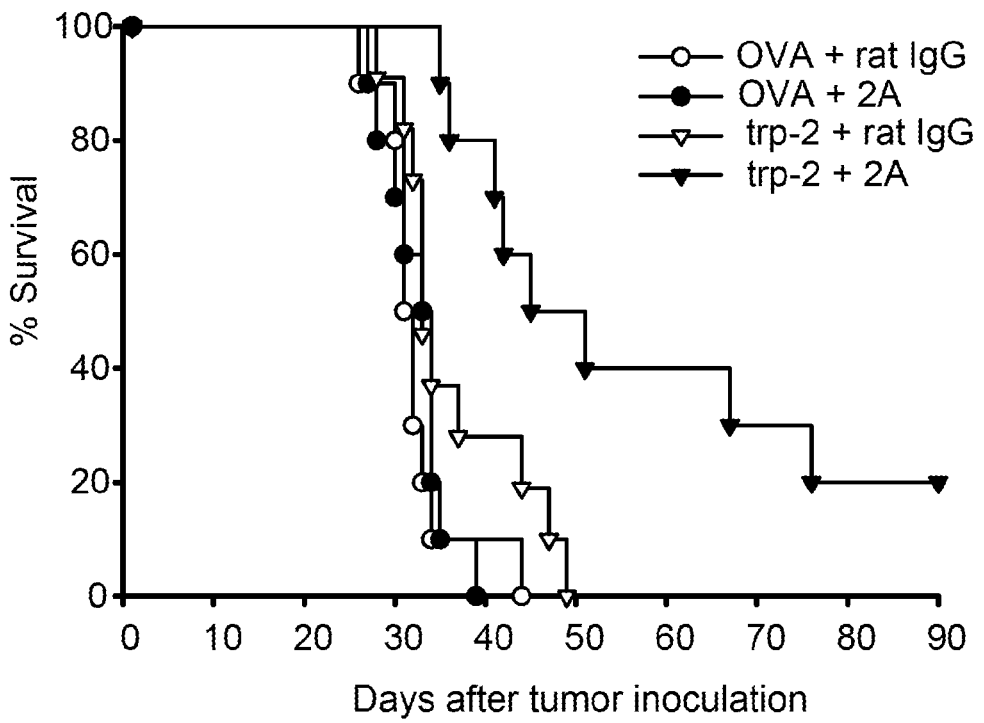

Effect of COPP Treatment in Metastasis Models of TC-1 Lung Cancer and B16-F10 Melanoma To determine the effect of COPP treatment more vigorously in other, poorly immunogenic tumors, two tumor models were tested. The TC-1 tumor line is derived from primary lung epithelial cells co-transformed with both the HPV-16 E6, HPV-16 E7 and ras oncogenes [Liu et al. (1996) Cancer Res. 56:21-6]. Therefore, the E7 peptide could be used as an immunogen. B16-F10 is a highly metastatic melanoma line, which presents the $H-2K^b$-restricted trp-2 peptide [Dranoff et al. (1993) Proc. Natl. Acad. Sci. USA 90:3539-3543; Bloom et al. (1997) J. Exp. Med. 185:453-459; Schreurs et al. (2000) Cancer Res. 60:6995-7001]. B6 mice were injected intravenously (i.v.) with $10^4$ TC-1 cells to establish lung metastases. Three days after tumor injection, the mice were injected s.c. with the E7 peptide and i.p. with the 2A mAb (COPP). As was observed with the C3 tumor, the administration of mAb 2A alone was insufficient to prolong survival in the tumor-bearing mice, as all of the mice died within 20 days. E7 peptide immunization alone did prolong survival, although all of the mice were dead by day 35. COPP treatment led to a significant survival advantage in that all of the mice which had received both the E7 peptide and mAb 2A survived at least 35 days, the time by which all the mice in the control groups had died (FIG. 7A). Twenty percent of the mice receiving both the E7 peptide and mAb 2A (COPP) were long-term survivors. In a second model, mice were injected i.v. with $10^5$ B16-F10 cells and treated with COPP three days later. As before, treatment by either mAb 2A or the trp-2 peptide alone was ineffective. However, COPP treatment (trp-2 peptide and mAb 2A) led to a significant survival advantage for all the mice and long-term survival (>90 days) in 20% of treated mice (FIG. 7B). Therefore, combined treatment with an antigenic, MHC class I restricted peptide and anti-4-1BB mAb (COPP) may be therapeutic for established, poorly immunogenic tumors.

Example 6

MAb 2A Enhances the Therapeutic Effect of a Dendritic Cell Vaccine

In order to determine whether an agonistic mAb specific for murine 4-1 BB (mAB 2A) enhances the anti-tumor immune response stimulated by DC-based vaccines, a murine model of squamous cell carcinoma of the head and neck was exploited. A poorly immunogenic murine (B6) squamous cell carcinoma line (SCCVII) was used for these experiments. DC were prepared as described above. The DC were "primed" with tumor antigen by culturing DC ($5 \times 10^6$ per well) with irradiated SCCVII cells ($1 \times 10^6$ well) in the wells of 24-well tissue culture plates for 24 hours. Four groups of five mice were injected s.c. (in the flank) with $2 \times 10^5$ SCCVII cells. Four days following injection of the tumor cells, the four groups of animals were injected s.c. in the contralateral flank with the following test vaccines:

Group 1: DCs primed with irradiated SCCVII ($1 \times 10^6$ DC and $3 \times 10^6$ irradiated SCCVII) and Rat IgG (100 µg)

Group 2: DCs primed with irradiated SCCVII ($1 \times 10^6$ DC and $3 \times 10^6$ irradiated SCCVII) and 2A mAb (100 µg)

Group 3: Rat IgG (100 µg) alone

Group 4: 2A mAb alone (100 µg) alone.

Figure 8:
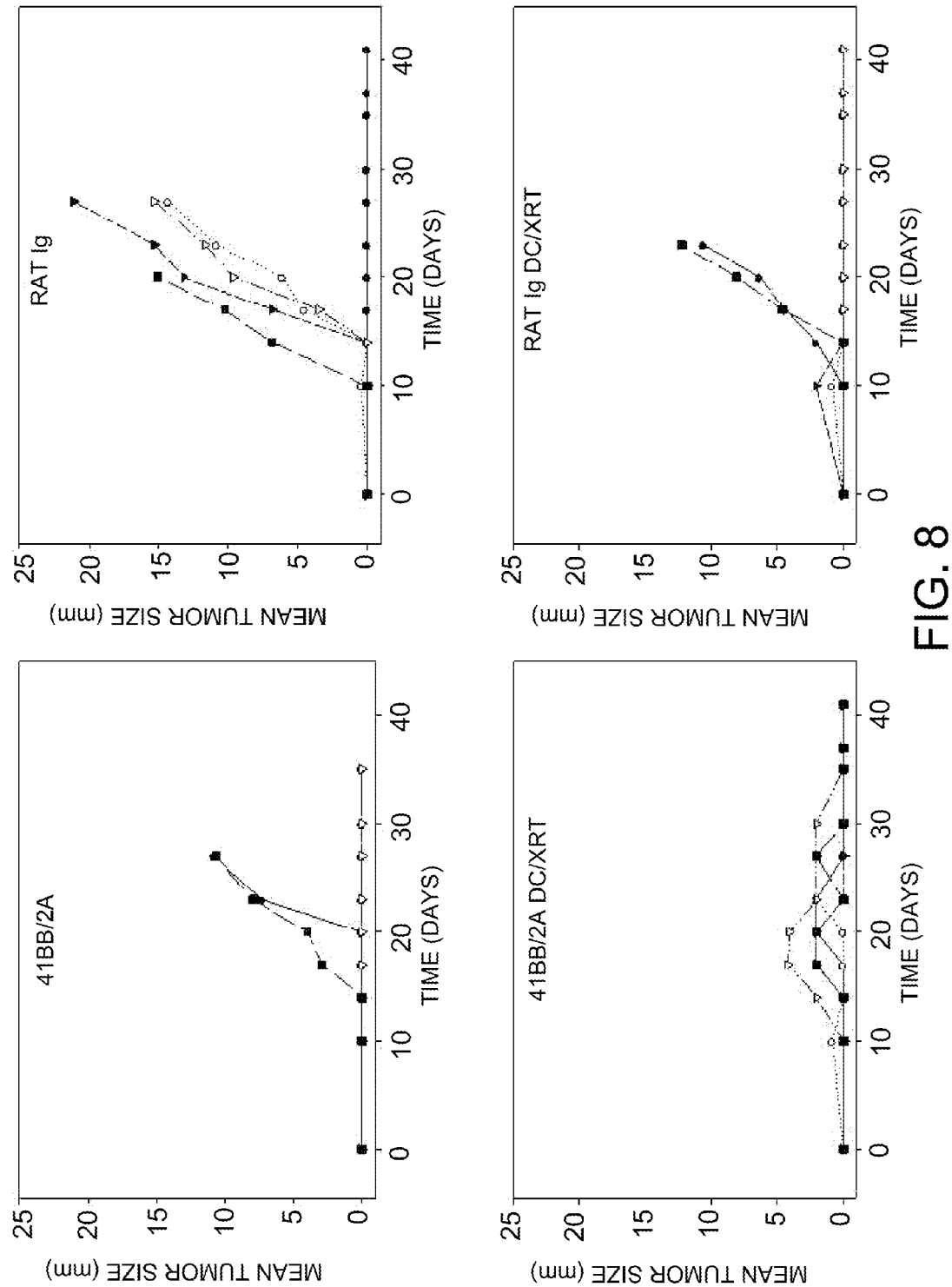
FIG. 8 is a series of line graphs showing the growth of tumors in mice injected s.c. (in one flank) with SCCVII tumor cells on day 0. On day 4, the mice were divided into four groups (5 mice per group) that were treated as follows. On days 4 and 11, the mice in the first two groups were injected s.c. in the contralateral flank with dendritic cells "primed" in vitro with SCCVII cells (bottom panels). On days 4, 7, 11 and 14, the mice in the first group were injected i.p. with 100 μg of rat IgG (bottom right panel; "RAT Ig DC/XRT") and the mice in the second group were injected i.p. with 100 μg of mAb 2A (bottom left panel; "4 1BB/2A DC/XRT"). On days 4, 7, 11, and 14 the mice in third and fourth group were injected with 100 μg of rat IgG (top right panel; "RAT Ig") and 100 μg of mAb 2A (top left panel; "4 1 BB/2A"), respectively. Tumor size (mean diameter; "Mean Tumor Size") was monitored. Each line in the graphs represents a single mouse.

The mice received the test vaccines twice, the second vaccination being a week after the first. In addition to being administered as a component of the vaccine, the 2A mAb (or control rat IgG) was administered three days after each test vaccination. Tumor growth was measured in a blinded fashion to determine therapeutic efficacy. As shown in FIG. 8, 80% of animals treated with rat IgG alone developed tumors (group 3; FIG. 8 top right panel). In animals treated with tumor "primed" C and rat IgG (group 1; FIG. 8, bottom right panel) or mAb 2A alone (group 4; FIG. 8, top left panel) there was therapeutic efficacy in 3 out of 5 mice. However, the most pronounced therapeutic effects were observed in animals treated with tumor "primed" DC and mAb 2A (group 2; FIG. 8, bottom left panel) in which all mice showed tumor regression. These data clearly demonstrate that antibody specific for 4-1BB is synergistic with tumor "primed" DC vaccines in stimulating therapeutic anti-tumor immunity.

Example 7

Development of Mouse anti-human 4-1BB MAbs

In order to generate agonistic mAbs specific for human 4-1BB, a strategy similar to that described above for generation of mAbs specific for murine 4-1BB was used. A soluble 4-1BB fusion protein composed of an extracellular fragment of human 4-1BB and the CH3-CH3 domain of human IgG1 was engineered. Mice immunized with this fusion protein produced polyclonal antibodies to 4-1BB. Spleens from these animals were fused with SP2/0 mouse myelomas to produce hybridomas that were screened by fluorescence flow cytometry with 293 cells transfected with cDNA encoding human 4-1BB. Two hybridomas (5.9 and 5.10) producing IgG1 mAbs showed human 4-1BB-specific staining.

Example 8

T Cell Costimulatory Ability of Mouse anti-Human 4-1BB MAbs

Figure 9:
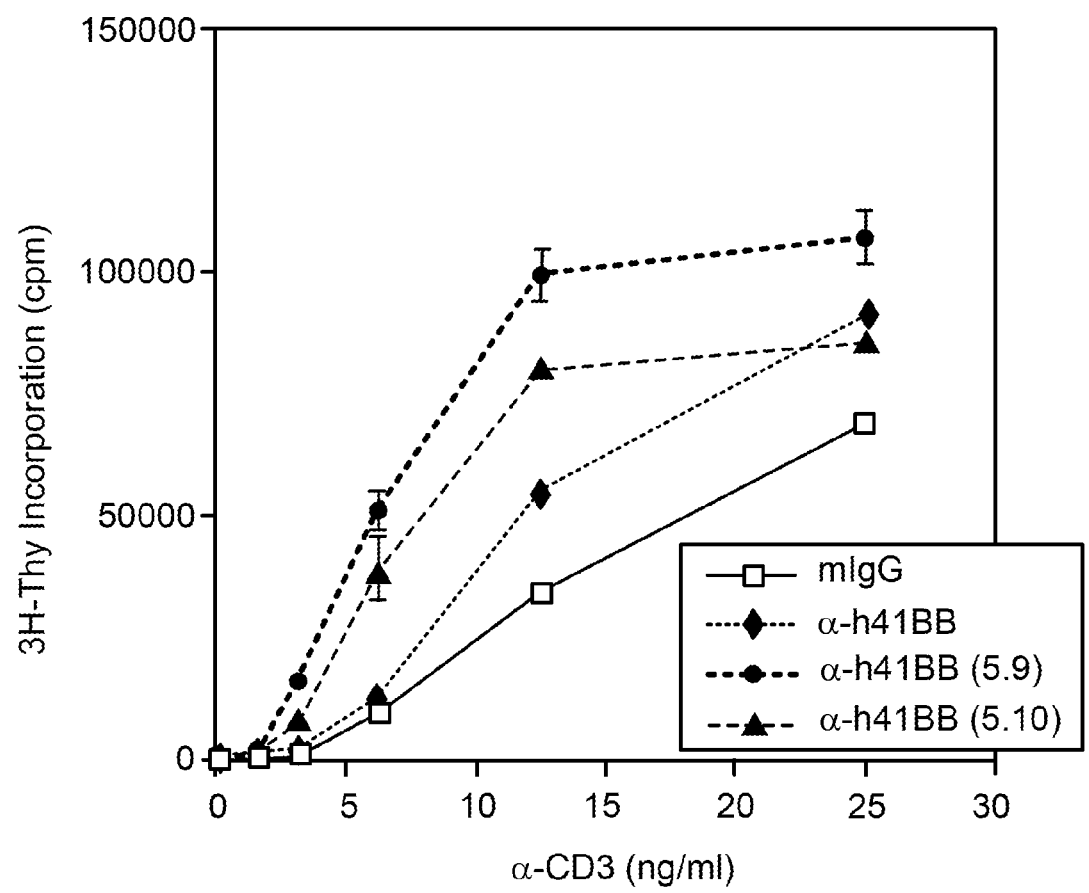
FIG. 9 is a line graph showing the proliferation ("$^3$H-Thy incorporation") in counts per minute ("cpm") of nylon wool purified human T cells stimulated with antibody specific for human CD3 (coated onto well-bottoms of 96-well tissue culture plates at the indicated concentrations) and either mAb 5.9 ("α-h41BB (5.9)"), mAb 5.10 ("α-h41 BB (5.10)"), a commercially available antibody specific for human 4-1BB ("α-h41BB"), or mouse IgG ("mIgG"), each coated onto the well-bottoms of 96-well tissue culture plates at a concentration of 10 μg/ml.

In order to determine whether the two anti-human 4-1BB mAbs described in Example 7 have the ability costimulate a T cell response, a standard in vitro costimulation assay was performed. Briefly, purified human T-cells were cultured with (a) antibody specific for human CD3 coated onto the well-bottoms of 96-well tissue culture plates at various concentrations and (b) varying concentrations of the 5.9 mAb, the 5.10 mAb, or normal mouse IgG, all also coated (at a concentration of 10 μg/ml) onto the well-bottoms of the 96-well tissue culture plates. $^3$H-TdR incorporation measured after a 48-hour culture period was used to determine T cell proliferation. (FIG. 9). Both anti-human 4-1BB stimulated significant T cell proliferation, thereby demonstrating the T cell costimulatory potential of these antibodies.

Example 9

MAb Enhances the Therapeutic Effect of Recombinant GM-CSF-Expressing Irradiated Tumor Cell Vaccine Experiments were performed in order to determine whether an agonistic mAb specific for murine 41-BB (mAb 2A) enhances the anti-metastatic immune response stimulated by irradiated tumor cells expressing a recombinant cytokine. Four groups of five B6 mice were injected i.v. with $5\times10^5$ B16-F10 melanoma cells in order to generate disseminated metastases. On days 3, 7, and 11 the mice were immunized s.c. with $4\times10^6$ irradiated B16-F10 cells stably transfected with and expressing cDNA encoding murine GM-CSF (B16-GM-CSF) and on days 4, 7, 10, 12, and 15 the mice injected i.p. with 100 μg of either rat IgG or mAb 2A as indicated below. The B16-GM-CSF cells were generated essentially as described in Dranoff et al. (1993) Proc. Natl. Acad. Sci. USA 90:3539-3543.

Figure 10:
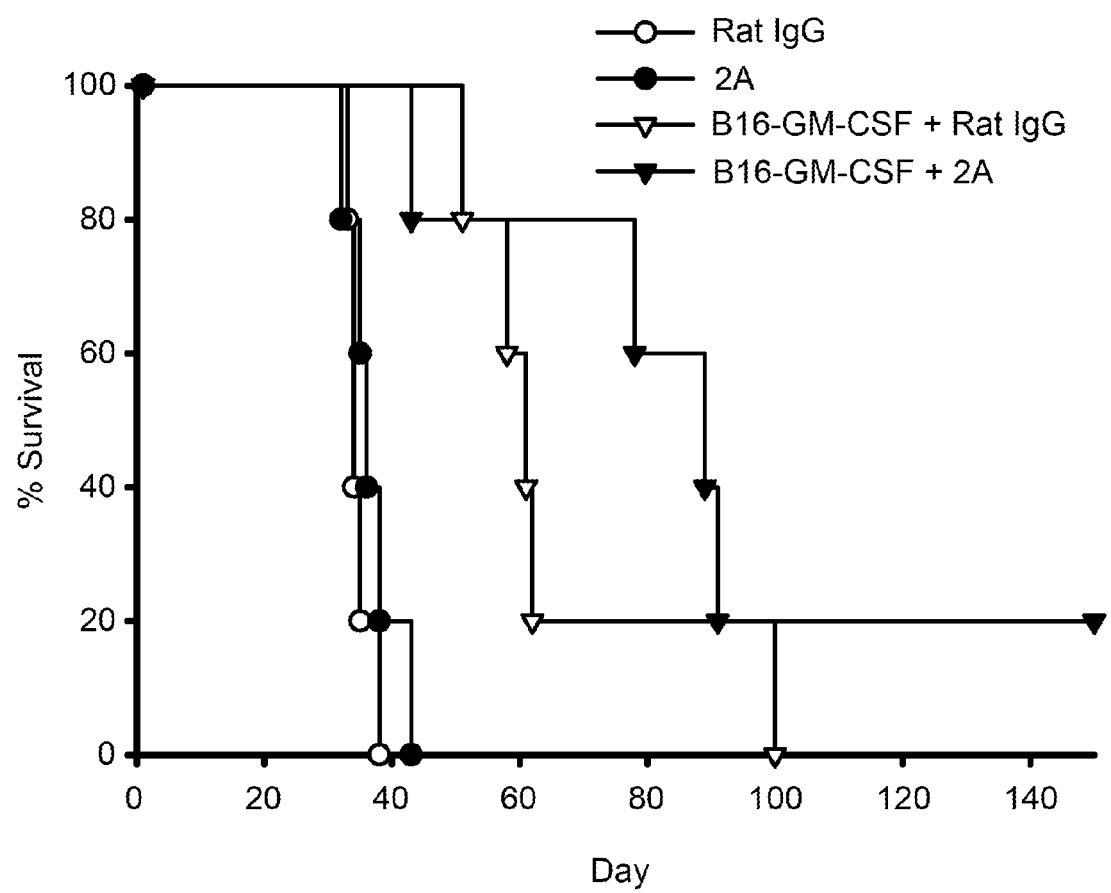
FIG. 10 is a survival curve showing the survival ("% Survival") of B6 mice treated as follows. Mice were injected intravenously (i.v.) with $5\times10^5$ B16-F10 cells on day 0. On days 3, 7, and 11 the mice were injected s.c. with irradiated B16-F10 cells expressing recombinant GM-CSF (triangles) or were not treated (circles). On days 4, 7, 10, 12, and 15, the mice were injected with 100 μg of either the 2A mAb ("2A") (filled circles and triangles) or rat IgG (unfilled circles and triangles). The mice were observed daily for the duration of the experiment.

Group 1: rat IgG only
Group 2: mAb 2A only
Group 3: B16-GM-CSF and rat IgG
Group 4: B16-GM-CSF and mAb 2A The mice were monitored for survival (FIG. 10). Mice immunized with B-16-GM-CSF and mAb 2A showed enhanced survival over mice immunized with B16-GM-CSF and rat IgG.

Example 10

Induction of Anergy in CD8$^+$ OT-1 T cells Following Intravenous Administration of OVA Peptide Intravenous (i.v.) delivery of antigen is an established approach to induce anergy in CD4$^+$ T cells [Valujskikh et al. (2001) Transplantation 72:685-693; Thorstenson et al. (2001) J. Immunol. 167:188-195; and Bercovici et al. (1999) Eur. J. Immunol. 29:345-354]. Following i.v. injection of antigen, antigen-specific T cells exposed to a high dose of soluble antigen become unresponsive to the antigen; this is demonstrated by the inability of the T cells to proliferate and secrete IL-2 upon exposure to the antigen in vitro in the presence of APC [Jacobs et. al. (1994) Immunology 82:294-300]. This approach was adapted by the inventors to examine the induction of anergy in CD8$^+$ T cells.

Figure 11:
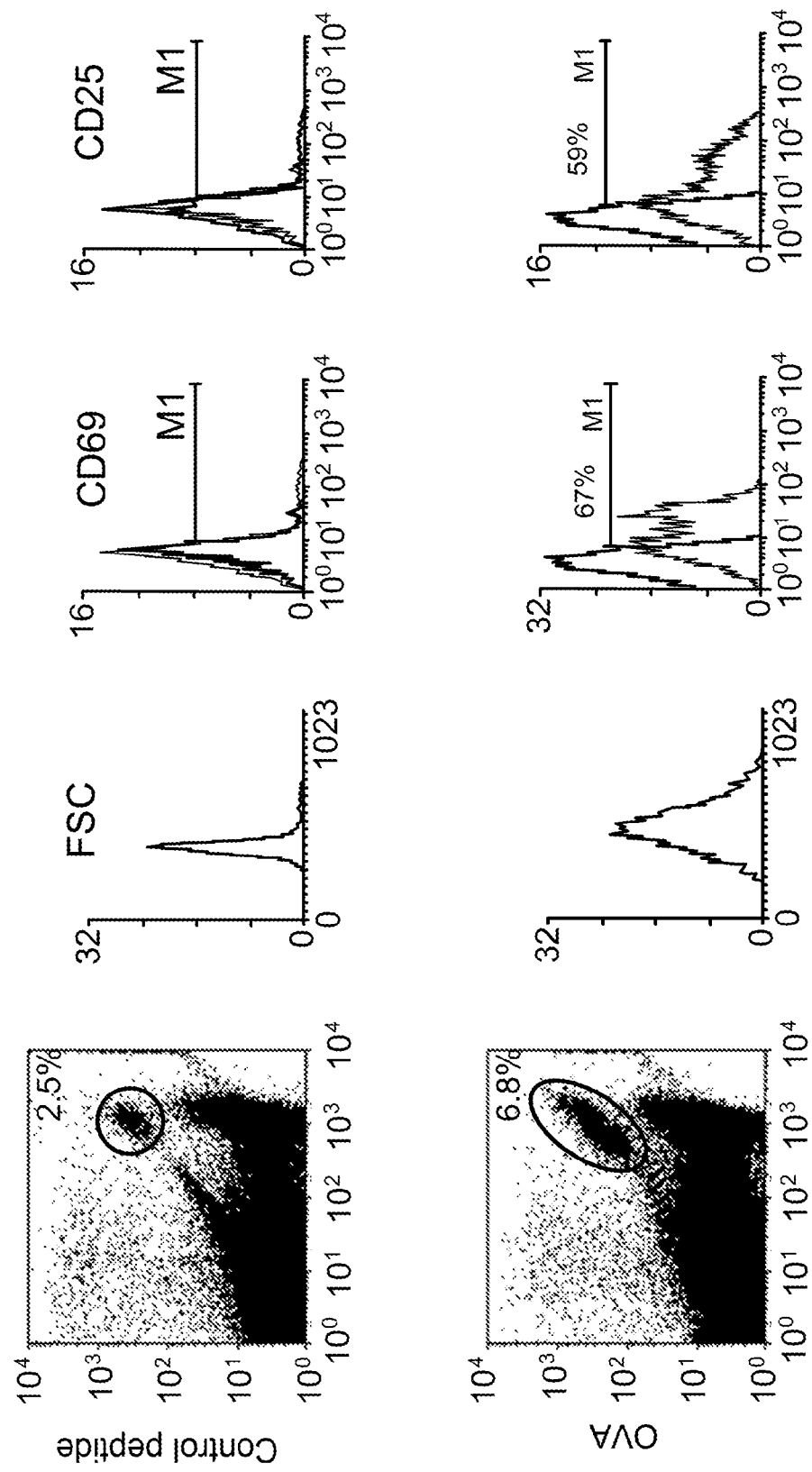
FIG. 11 is a series of one- and two-dimensional FFC histograms showing the forward light scatter ("FSC") and the relative proportion of CD69-expressing CD25-expressing cells in CD8+, OVA tetramer+pooled lymph node and splenic T cells from C57BL/6 (B6) mice that had been injected with OT-1 transgenic mouse lymphoid cells and either a control peptide (top histograms) or the OVA peptide (bottom histograms). The two-dimensional FFC histograms (left panels) show the relative numbers of CD8-expressing cells (x-axis) and OT-1 transgenic T cell receptor (TCR)-expressing (OVA tetramer+) (y-axis). Cells expressing CD8 and the transgenic OT-1 TCR were gated (as indicated by the circle in the top two-dimensional FFC histogram and the ellipse in the bottom two-dimensional FFC histogram) and the gated populations were analyzed for FSC (shown in the first one-dimensional FFC histograms) and the relative proportions of CD69-expressing cells (shown in the second one-dimensional FFC histograms) and CD25-expressing cells (shown in the third one-dimensional FFC histograms). The numbers in the two-dimensional FFC histograms indicate the proportions of CD8-expressing, OT-1 transgenic TCR-expressing cells in the pooled lymph node and spleen cells from the two groups of mice.

The intravenous administration of a H-2K$^b$-restricted peptide epitope of ovalbumin (the "OVA peptide") [Deeths et al. (1999) J. Immunol. 163:102-110] to B6 mice to which OT-1 T cells had previously been adoptively transferred, led to the activation and clonal expansion of the OT-1 T cells. Two days after peptide administration, pooled lymph node and spleen cells from mice that had received a control peptide or the OVA peptide were stained with both anti-CD8 antibody and tetrameric H-2K$^b$-OVA (OVA tetramer). Whereas only 2.5% of the CD8$^+$ T cells were OVA tetramer-positive (i.e., were OT-1 T cells) in the mice treated with control peptide, the proportion of CD8$^+$ T cells that were OT-1 T cells in the OVA-treated mice was 6.8% (FIG. 11). OT-1 cell blastogenesis was also observed in the OVA-treated mice, as demonstrated by the increase in forward scatter of the cells from these mice by FACS analysis. Furthermore, more than 50% of the OT-1 cells in the OVA-treated mice expressed the T-cell activation markers, CD69 and CD25 (FIG. 11).

Figure 12A:
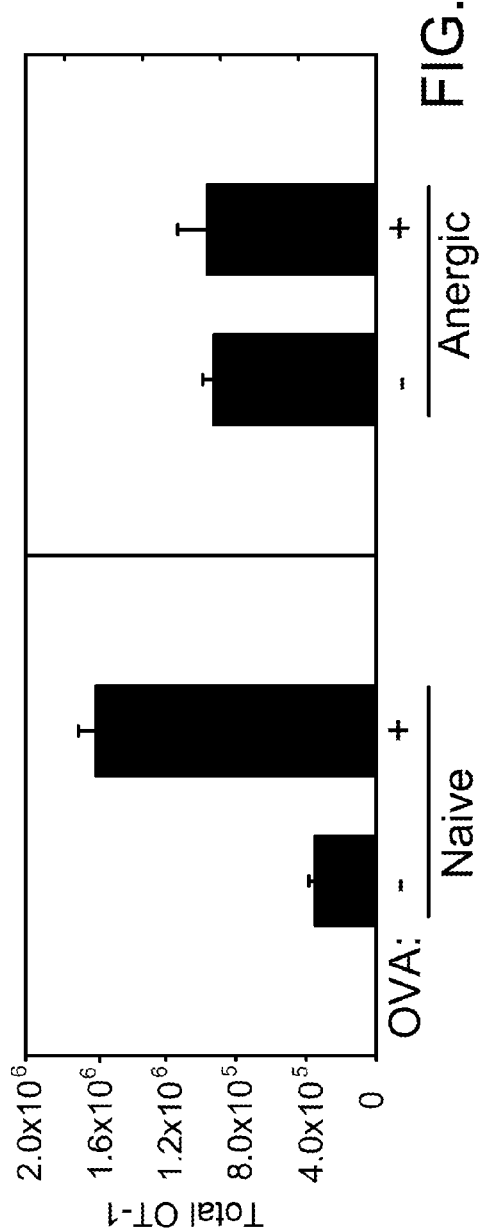
FIG. 12A is a pair of bar graphs showing means (and standard deviations) of the total numbers ("Total OT-1") of OT-1 transgenic TCR-expressing cells in pooled lymph node and spleen cells from individual B6 mice (3 per group) that were injected with OT-1 transgenic mouse lymphoid cells and either phosphate buffered saline (PBS) (left panel; "Naïve") or the OVA peptide (right panel; "Anergic"), followed ten days later by a challenge with either a control peptide ("−") or the OVA peptide ("+"). The mice were sacrificed, the spleens and lymph nodes removed, and pooled cell suspensions prepared separately from each mouse two days after the challenge. The cells were analyzed for expression of the OT-1 transgenic TCR and CD8 by FFC and the total numbers of OT-1 transgenic TCR-expressing cells in the various cell preparations were calculated.
Figure 12C:
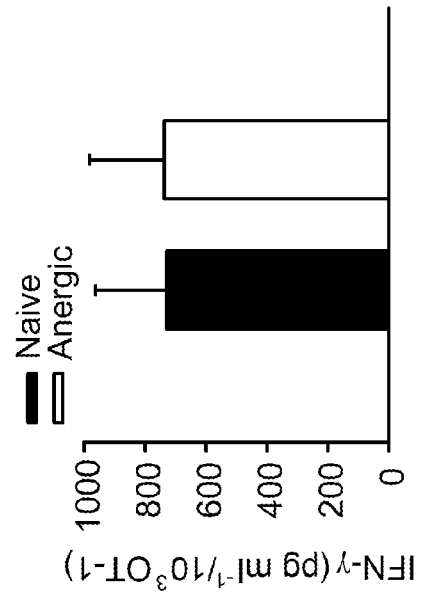
FIG. 12C is a bar graph showing the amount of interferon-γ (IFN-γ) (pg per ml per 1,000 OT-1 transgenic TCR-expressing cells) produced (after culturing for 72 hours in the presence of the OVA peptide) by the anergic (unfilled bar) and naïve (filled bar) cells described for FIG. 12A that had initially been injected with PBS ("Naïve") or the OVA peptide ("Anergic") and then challenged with the OVA peptide.
Figure 12B:
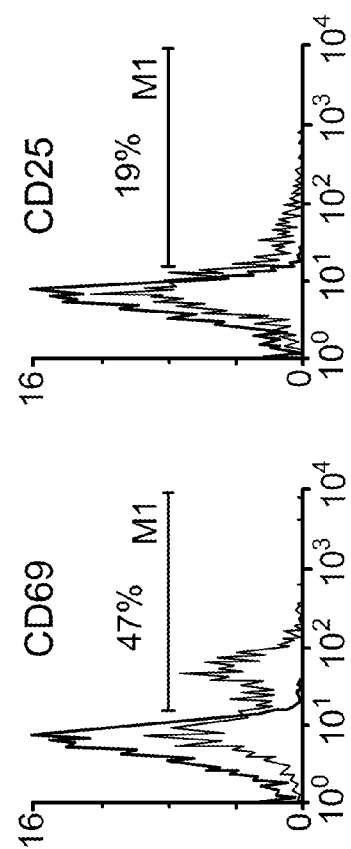
FIG. 12B is a pair of FFC histograms showing the relative proportions of CD69—(left panel) and CD25—(right panel) expressing cells from the mice described for FIG. 12A that had received an initial injection of and been challenged with the OVA peptide. Cells stained with CD69 or CD25 are shown by the unfilled profiles and those stained with an isotype control antibody are shown by the filled profiles.

To determine the responsiveness of OT-1 T cells after i.v. exposure to OVA peptide, B6 mice treated as described above were rechallenged i.v. 10 days later with either a control peptide or the OVA peptide. For comparison, naïve mice (i.e., mice that had not received the initial injection of OVA peptide) were also injected with either the control peptide or OVA peptide. Two days following peptide administration, spleens and lymph nodes were harvested from the mice and the total numbers of OT-1 cells in pooled spleen and lymph node samples were determined by OVA tetramer staining. A greater than 4-fold expansion was observed in the naïve mice treated with OVA. In contrast, no significant expansion of OT-1 cells resulted from rechallenge with OVA in those mice that had received OVA ten days previously (FIG. 12A), thus suggesting the induction of OT-1 T cell anergy by the intial exposure to OVA. Unlike naive OT-1 T cells, in which the expression of CD69 and CD25 could be induced following antigenic challenge, the majority of anergic OT-1 T cells failed to express significant levels of CD25 following antigenic challenge, although significant expression of CD69 was observed (FIG. 12B).

In order to determine whether or not OT-1 cells retained their effector function following the induction of anergy, splenocytes from B6 mice injected with OT1 T cells and a single dose of OVA as described above were restimulated with OVA peptide in vitro. Although the OT-1 cells pre-exposed to OVA were incapable of proliferating in vivo, they secreted IFN-γ upon restimulation with OVA in vitro at a level similar to naïve OT-1 T cells (FIG. 12C). These results indicate that anergic OT-1 T cells retained the ability to secrete IFN-γ upon restimulation.

Example 11

CD137 Signaling Prevents the Induction of OT-1 T Cell Anergy

Figure 13A:
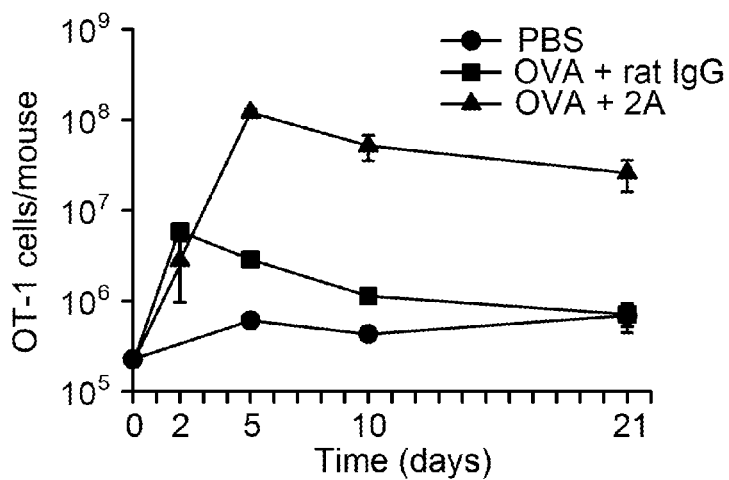
FIG. 13A is a line graph showing the means (and standard deviations) of the total numbers of OT-1 transgenic TCR-expressing cells ("OT-1 cells/mouse") in pooled lymph node and spleen cells from individual B6 mice (3 mice per group) at various times ("Time (days)") after injection with OT-1 transgenic mouse lymphoid cells and either PBS or the OVA peptide ("OVA"). On the day of OVA peptide (or PBS) injection, and again three days later, the mice were injected with either control rat IgG ("rat IgG") or anti-CD137 monoclonal antibody (mAb) ("2A").

Following adoptive transfer of OT-1 cells into naïve B6 mice and the administration of OVA peptide, mice were injected i.p. with either a CD137 mAb (clone 2A) or control rat IgG. Mice were sacrificed at various time points up to 21 days following injection of the OVA peptide and the total number of OT-1 cells present in the spleens and lymph nodes in each group of mice was determined by OVA tetramer staining. As shown in FIG. 13A, treatment with anti-CD137 mAb following OVA administration led to an approximately ten-fold increase in the number OT-1 cells compared to those mice that received the control rat IgG. This robust T cell response following CD137 mAb injection led to significant splenomegaly in the CD137 mAb treated mice (data not shown). In contrast, the T cell response in the mice given the control rat IgG peaked 2 days following OVA administration and rapidly declined, reaching baseline by day 21. OT-1 cells in the anti-CD137 mAb treated mice persisted for at least 21 days following antigenic stimulation. These data demonstrate the ability of CD137 stimulation to promote the expansion of OT-1 T cells in vivo.

Figure 13B:
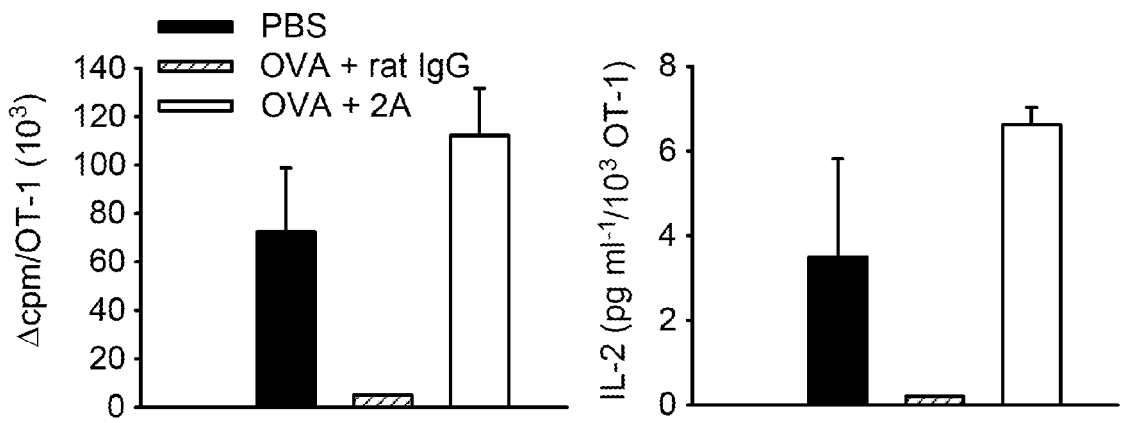
FIG. 13B is a pair of bar graphs showing the relative proliferation in vitro (left panel) and amount of interleukin-2 (IL-2) (right panel) produced in vitro by spleen cells prepared from the individual B6 mice (3 mice per group) described for FIG. 13A 10 days following injection with the OVA peptide (or PBS). The numbers of OT-1 transgenic TCR-expressing cells in the spleen cell preparations were calculated and the data for proliferation are expressed as means (and standard deviations) of the counts per minute (cpm) of [$^3$H]-thymidine incorporated per 1,000 OT-1 transgenic TCR-expressing cells in the assay cultures ("Δcpm/OT-1 ($10^3$)") and the data for IL-2 production are expressed as the means (and standard deviations) of the amounts (in pg/ml) of IL-2 produced per OT-1 transgenic TCR-expressing cell ("IL-2 (pg ml$^{-1}$/$10^3$ OT-1") in the assay cultures.
Figure 13C:
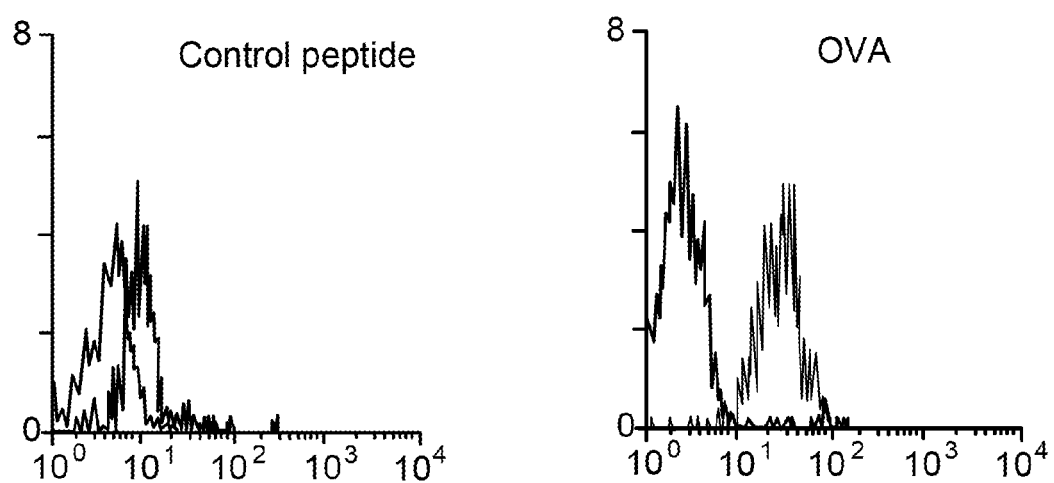
FIG. 13C is a pair of FFC histograms showing the relative proportion of cells staining with an anti-VLA mAb (unfilled profiles) or isotype control mAb (filled profiles) in spleen cells from the mice described for FIG. 13A that had been injected with the OVA peptide after a challenge (ten days after the initial injection with the OVA peptide) with the OVA peptide (right panel) or a control peptide.

To determine the effect of CD137 signaling on induction of T cell anergy, mice to which OT-1 T cells had been adoptively transferred and that were injected with either PBS, OVA peptide and anti-CD137 mAb, or OVA peptide and control rat IgG were sacrificed ten days following peptide (or PBS) administration. The number of OT-1 cells present in the pooled splenocytes from each group of mice was determined by OVA tetramer staining. The splenocytes were subsequently restimulated in vitro with an optimal concentration of OVA peptide. OT-1 proliferation and IL-2 secretion were measured 72 and 48 hours later, respectively. The proliferation of OT-1 T cells, as measured by [$^3$H]-thymidine incorporation, was determined on a per cell basis. Unlike the naïve OT1 T cells from mice that had received PBS, OT-1 cells from mice that were given the OVA peptide and control rat IgG failed to proliferate following in vitro restimulation (FIG. 13B). Furthermore, FACS analysis demonstrated that virtually 100% of the OT-1 T cells from the mice previously exposed to OVA peptide expressed the late activation marker VLA-4, in contrast to the OT-1 cells in the control peptide-treated mice (FIG. 13C). In sharp contrast, proliferation was observed in OT-1 T cells from those mice that received anti-CD137 mAb and OVA peptide. IL-2 production was not observed following restimulation of the anergic OT-1 cells from OVA peptide and anti-CD137 mAb treated mice, a finding consistent with their lack of proliferation (FIG. 13B) whereas OT-1 cells from the anti-CD137 treated mice secreted IL-2 to an extent comparable with naïve OT-1 (FIG. 3B); this finding provided further evidence that CD137 signaling prevented the induction of T cell anergy.

Example 12

CD137 Signaling Reverses OT-1 T Cell Anergy

Figure 14A:
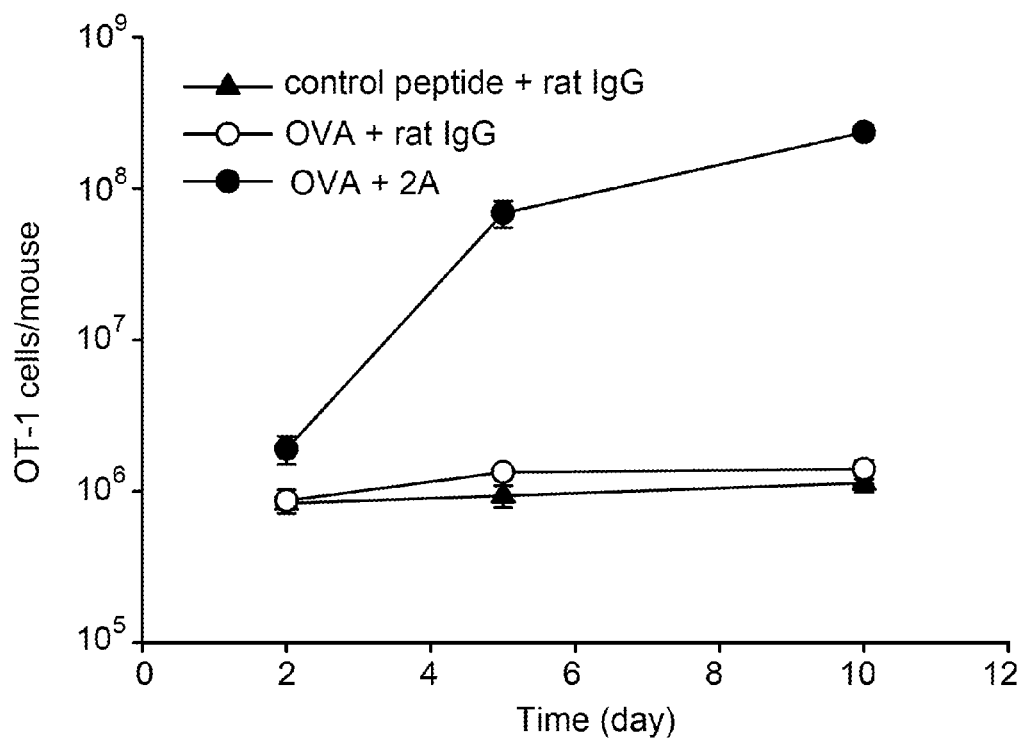
FIG. 14A is a line graph showing the means (and standard deviations) of the total numbers of OT-1 transgenic TCR-expressing cells ("OT-1 cells/mouse") in pooled lymph node and spleen cells from individual B6 mice (3 mice per group) that had been injected with OT-1 transgenic mouse lymphoid cells and the OVA peptide and ten days after the OVA peptide injection challenged with either the OVA peptide ("OVA") or a control peptide ("control peptide") and injected with either control rat IgG ("rat IgG") or anti-CD137 monoclonal antibody (mAb) ("2A"). Assays were performed at the indicated days after the challenge ("Time (day)").

Experiments were performed to determine whether CD137 signaling could reverse anergy in an already anergic T cell. To address this question, naïve B6 to which OT-1 T cells had been adoptively transferred mice were injected i.v. with OVA peptide as described above in order to induce anergy in the OT-1 T cells. Ten days later, the mice were injected i.p. with anti-CD137 mAb together with OVA peptide. Mice were sacrificed 2, 5 and 10 days following treatment and the total number of OT-1 T cells was determined by OVA tetramer staining. As shown in FIG. 14A, a marked expansion of the OT-1 cells was observed in OVA-exposed mice that were treated with anti-CD137 mAb and OVA peptide. The anergic OT-1 cells, however, failed to expand following a subsequent challenge with either the OVA peptide or control peptide (FIG. 14A). These findings indicate that CD137 signaling, in addition to preventing the induction of T cell anergy, breaks anergy in OT-1 T cells that had been previously energized.

Figure 14B:
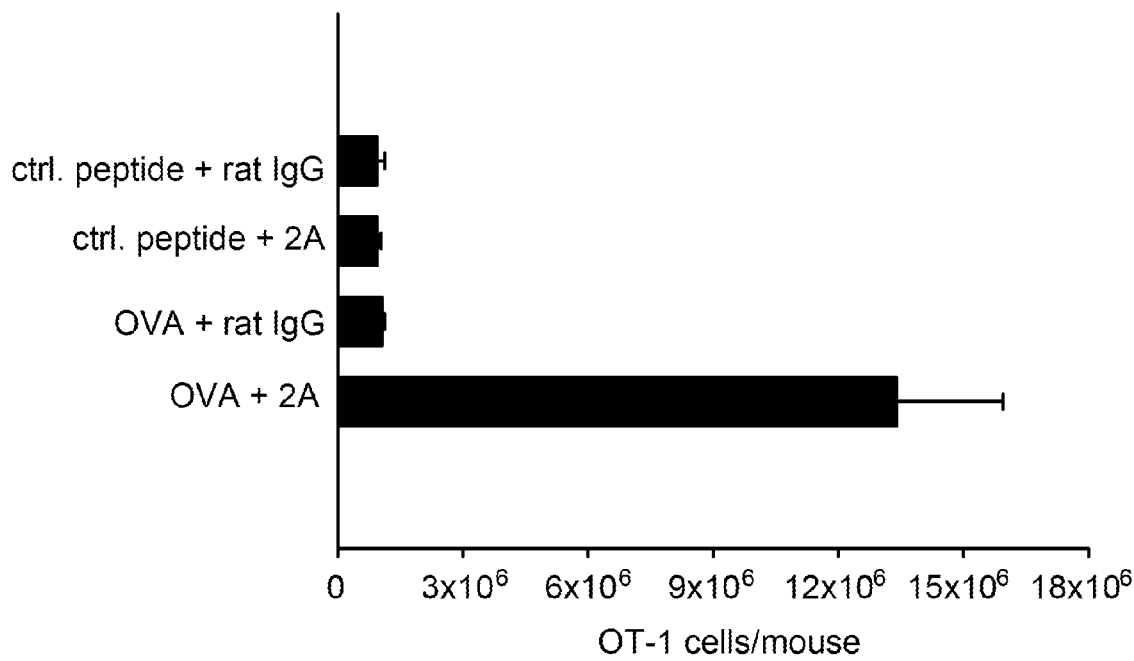
FIG. 14B is a bar graph showing the means (and standard deviations) of the total numbers of OT-1 transgenic TCR-expressing cells ("OT-1 cells/mouse") in pooled lymph node and spleen cells from individual B6 mice (3 mice per group) that had been injected with OT-1 transgenic mouse lymphoid cells and the OVA peptide and ten days after the OVA peptide injection challenged with the indicated combinations of the OVA peptide ("OVA") or a control peptide ("control peptide") and control rat IgG ("rat IgG") or anti-CD137 mAb ("2A"). The assay was performed 3 days after the challenges.
Figure 14C:
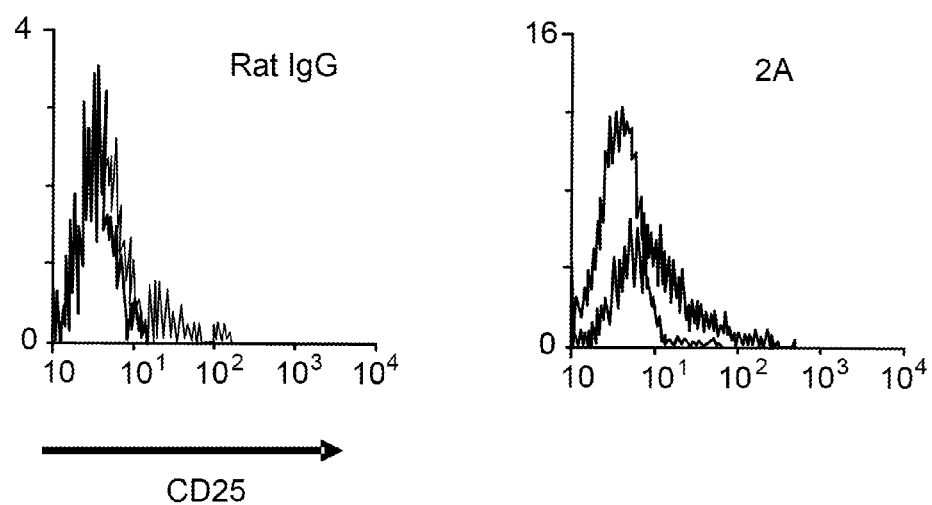
FIG. 14C is a pair of histograms showing the relative proportion of cells staining with an anti-CD25 mAb (unfilled profiles) or an isotype control mAb (filled profiles) in the cells from the mice described for FIG. 14B that were challenged with OVA and injected with either anti-CD137 mAb ("2A"; right panel) or control rat IgG ("rat IgG"; left panel).

While the above results indicate that anti-CD137 mAb together with OVA peptide can reverse anergy in OT-1 T cells, it is unclear whether signaling via the T cell receptor is absolutely necessary for anti-CD137 mAb to break anergy. To test this, the OVA peptide OT-1 T cell anergic mice were prepared as described above. Ten days after the injection of OVA peptide, the mice were given various combinations of control peptide or OVA peptide and control rat IgG or anti-CD137 mAb. Three days later, the mice were sacrificed and the total number of OT-1 cells determined. OT-1 cell expansion was only observed in the group of mice that received both OVA peptide and anti-CD137 mAb (FIG. 14B). Importantly, no OT-1 T cell proliferation was observed in the group of mice that received the control peptide and anti-CD137 mAb. As was shown above (FIG. 12B), anergic OT-1 cells failed to express CD25 following encounter with antigen. However, CD137 signaling restored, at least in part, the ability of these cells to express CD25 (FIG. 14C). These data show that reversal of anergy in CD8$^+$ T cells by CD137 mAb requires TCR engagement.

Figure 14D:
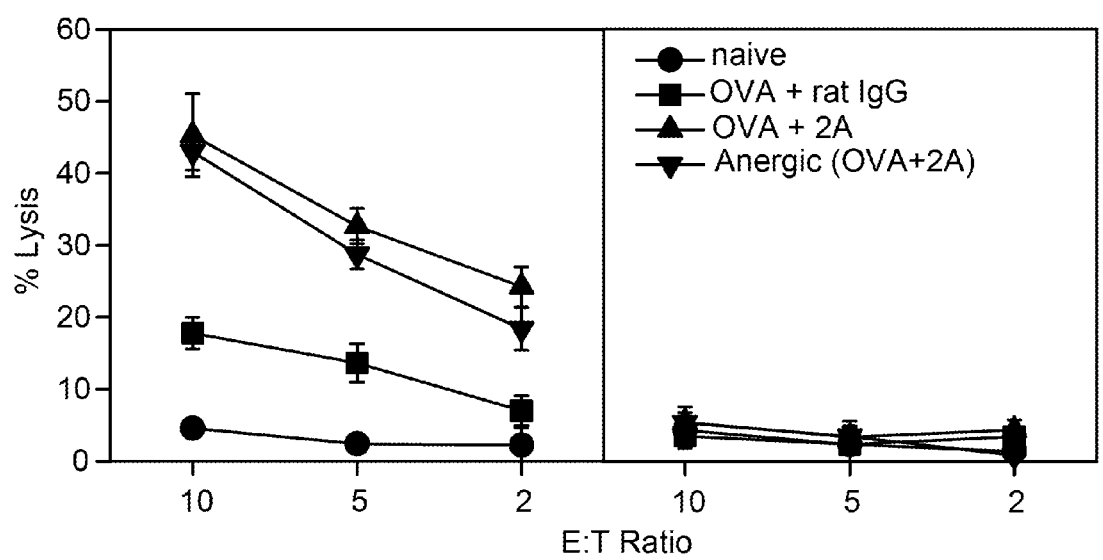
FIG. 14D is a pair of line graphs showing the cytotoxic activity ("% Lysis") of various cell populations against EL4 target cells pulsed with the OVA peptide (left panel) and control EL4 target cells (right panel). B6 mice were injected with OT-1 transgenic mouse lymphoid cells and the OVA peptide and ten days after the OVA peptide injection were challenged with the OVA peptide ("OVA") and injected with anti-CD137 mAb; five days after the challenge and mAb injection, cells expressing the OT-1 transgenic TCR were sorted by FACS and used as effector cells ("Anergic (OVA+ 2A)") in the cytotoxicity assays. Two control OT-1 transgenic TCR-expressing cell populations were also FACS sorted and tested. One population was from mice that had been treated identically to the first described population except that, instead of receiving an initial injection of the OVA peptide, the mice received an injection of a control peptide ("OVA+ 2A"). A second population was obtained from mice that had been treated identically to the first described population except that, instead of receiving an initial injection of the OVA peptide, the mice received an injection of a control peptide, and, instead of being injected with anti-CD137 mAb at the time of challenge with the OVA peptide, the mice were injected with control rat IgG ("OVA+rat IgG"). An additional control effector population consisted of OT-1 transgenic TCR-expressing cells sorted by FACS from spleen and lymph nodes of untreated OT-1 TCR transgenic mice ("Naïve").

Experiments were then carried out to test whether cytolytic activity of OT-1 T cells is retained by CD137 mAb exposure. OT-1 cells were sorted by FACS following staining with the OVA tetramer from the OVA-tolerized mice 5 days after challenge with OVA peptide and CD137 mAb and were used as effector cells in a standard 4-hour $^{51}$Cr-release assay for cytotoxicity against OVA-pulsed EL4 and control EL4 cells (FIG. 14D; "Anergic (OVA+2A)"). As controls, OT-1 cells were identically sorted from mice that, instead of initially being injected with the OVA peptide, were injected with the control peptide and then 10 days later were challenged with the OVA peptide and either rat IgG ("OVA+rat IgG") or anti-CD137 mAb ("OVA+2A"); the cell sorting cytotoxicity testing, as for the experimental group, were performed 5 days after the peptide challenge and mAb/control IgG treatment. As shown in FIG. 14D, approximately 20% specific lysis was observed at an E:T ratio of 10 to 1 in those mice that had received the control IgG. However, a more than two-fold increase in cytotoxicity was observed in OT-1 cells isolated from those mice that had received anti-CD137 mAb. Importantly, a similar level of cytotoxicity was observed in OT-1 cells isolated from both the naïve and the tolerized mice, provided they received anti-CD137 mAb, inidicating that anti-CD137 mAb not only restores proliferative capacity, but also cytotoxicity, in previously anergized OT-1 cells.

Example 13

CD137 Signaling in the Prevention and Reversal of P1A Peptide-Induced Tolerance in Tumor-specific T Cells A previously established tumor model was used to examine the effect of CD137 signaling in the prevention and reversal of T cell tolerance. P815R is a clonal variant of highly tumorigenic P815 mastocytoma, which unlike the parent P815 tumor, regresses spontaneously after inoculation into syngeneic DBA/2 mice [Nieland et al. (1999) J. Cell Biochem. 73:145-152]. Administration of a peptide epitope of P1A, a non-mutated self tumor antigen [Van den Eynde et al. (1991) J. Exp. Med. 173:1373-1384], in incomplete Freund's adjuvant (IFA) induces unresponsiveness of CD8+ T cells and promotes the progressive growth of the P815R tumor [Nieland et al. (1999) J. Cell Biochem. 73:145-152]. Subcutaneous injection of P815R cells into DBA/2 mice led to the transient development of subcutaneous tumors.

At day 40 after tumor inoculation, 80% of the mice that were treated with IFA alone were tumor-free (FIG. 15A, left panel). In contrast, only 10% of mice were tumor free following the administration of P1A peptide with control rat IgG ten days prior to tumor challenge (FIG. 15A, middle panel), suggesting that the injection of P1A peptide induced tolerance in P1A-specific CD8+ CTL. Treatment with anti-CD137 mAb together with P1A peptide prevented tumor development altogether in 50% of mice (FIG. 15A, right panel); however, tumor regression was observed in 40% of the mice that did develop tumors, suggesting that treatment with anti-CD137 mAb prevents the induction of P1A-induced T cell anergy.

To test for an effect of anti-CD137 mAb on the regression of established P815R tumor caused by P1A peptide-induced anergy, mice were first tolerized with P1A peptide in IFA for 10 days and were subsequently challenged with P815R cells. Three days following tumor challenge, mice were given control rat IgG or anti-CD137 mAb. In mice treated with the control rat IgG, 90% of the mice developed progressively growing tumors (FIG. 15B, left panel). In contrast, anti-CD137 mAb treatment led to tumor regression in 100% of mice (FIG. 15B, right panel). These findings indicate that CD137 signaling can prevent and break T cell anergy after the administration of a tolerogenic P1A peptide, leading to the regression of P815R tumors.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a subject that has, or is at high risk of developing, cancer, the method comprising administering to the subject a population of cells comprising an activated T cell obtained by a procedure comprising exposing in culture a cell sample comprising T cells to (i) an immunogenic stimulus, wherein the immunogenic stimulus comprises an immunogenic molecule produced by a tumor cell, or a peptide epitope of such a molecule, but does not comprise a tumor cell, and (ii) an agonistic antibody, or an antibody fragment, that binds to 4-1BB.

2. The method of claim 1, wherein the cells of the cell sample are from the subject.

3. The method of claim 1, wherein the subject is a human.

4. The method of claim 1, wherein the procedure comprises multiple exposures.

5. The method of claim 4, wherein the level of immune activity of exposed cells is tested after one or more exposures.

6. The method of claim 5, wherein the immune activity is cytotoxic T lymphocyte (CTL) activity.

7. The method of claim 5, wherein the immune activity is helper T cell activity.

8. The method of claim 1, wherein, prior to the procedure, the T cells in the cell sample are anergic.

9. The method of claim 1, wherein the cell sample comprises CD4+T cells, CD8+T cells, or CD4+T cells and CD8+T cells.

10. The method of claim 1, wherein the activated T cell exerts a neutralizing effect or a cytotoxic effect on tumor cells in the subject.

11. The method of claim 1, wherein the culture further comprises one or more cytokines or growth factors.

12. The method of claim 1, wherein the immunogenic stimulus comprises, a tumor cell lysate, a tumor-associated antigen (TAA), a peptide epitope of a TAA, or a heat shock protein bound to a peptide epitope of a protein expressed by a tumor cell.

13. The method of claim 12, wherein the TAA is a molecule produced by a cancer cell of a cancer selected from the group consisting of a leukemia, a lymphoma, a neurological cancer, a melanoma, a breast cancer, a lung cancer, a head and neck cancer, a gastrointestinal cancer, a liver cancer, a pancreatic cancer, a genitourinary cancer, a prostate cancer, a renal cell cancer, a bone cancer, and a vascular cancer.

14. The method of claim 1, wherein the immunogenic stimulus comprises
   (i) an antigen presenting cell (APC) comprising a major histocompatibility complex (MHC) molecule with a peptide-epitope bound thereto, wherein the peptide-epitope is a fragment of a TAA,
   (ii) an APC that has been incubated with tumor cells, a tumor cell lysate, a tumor-associated antigen (TAA), a peptide-epitope of a TAA, or a heat shock protein bound to a peptide-epitope expressed by a tumor cell, or
   (iii) a hybrid cell formed by fusing a cancer cell and an APC.

15. The method of claim 14, wherein the cytokine is granulocyte macrophage-colony stimulating factor (GM-CSF).

16. The method of claim 14, wherein the MHC molecule is a MHC class I molecule or a MHC class II molecule.

17. The method of claim 14, wherein the APC of (i), (ii), or (iii) is a dendritic cell.

18. The method of claim 14, wherein the cancer cell is of a cancer selected from the group consisting of a leukemia, a lymphoma, a neurological cancer, a melanoma, a breast cancer, a lung cancer, a head and neck cancer, a gastrointestinal cancer, a liver cancer, a pancreatic cancer, a genitourinary cancer, a prostate cancer, a renal cell cancer, a bone cancer, and a vascular cancer.

* * * * *

UNITED STATES PATENT AND TRADEMARK OFFICE
CERTIFICATE OF CORRECTION

PATENT NO.         : 8,772,026 B2                                   Page 1 of 1
APPLICATION NO.    : 13/426151
DATED              : July 8, 2014
INVENTOR(S)        : Lieping Chen and Scott E. Strome It is certified that error appears in the above-identified patent and that said Letters Patent is hereby corrected as shown below:

Title Page, Item (54), and in the Specification, Column 1, line 2, please delete "4-1 BB" and insert -- 4-1BB --, therefor.

Signed and Sealed this
Twenty-fifth Day of November, 2014

Michelle K. Lee
*Deputy Director of the United States Patent and Trademark Office*

SEQUENCE LISTING

```
<160> NUMBER OF SEQ ID NOS: 12

<210> SEQ ID NO 1
<211> LENGTH: 25
<212> TYPE: PRT
<213> ORGANISM: Homo sapiens

<400> SEQUENCE: 1

Met Ala Ile Ser Gly Val Pro Val Leu Gly Phe Phe Ile Ile Ala Val
1               5                   10                  15

Leu Met Ser Ala Gln Glu Ser Trp Ala
            20                  25

<210> SEQ ID NO 2
<211> LENGTH: 5
<212> TYPE: PRT
<213> ORGANISM: Homo sapiens

<400> SEQUENCE: 2

Lys Phe Glu Arg Gln
1               5

<210> SEQ ID NO 3
<211> LENGTH: 15
<212> TYPE: PRT
<213> ORGANISM: Homo sapiens

<400> SEQUENCE: 3

Met Asp Asp Gln Arg Asp Leu Ile Ser Asn Asn Glu Gln Leu Pro
1               5                   10                  15

<210> SEQ ID NO 4
<211> LENGTH: 4
<212> TYPE: PRT
<213> ORGANISM: Homo sapiens

<400> SEQUENCE: 4

Lys Asp Glu Leu
1

<210> SEQ ID NO 5
```

```
<211> LENGTH: 8
<212> TYPE: PRT
<213> ORGANISM: Human immunodeficiency virus 1

<400> SEQUENCE: 5

Arg Lys Lys Arg Arg Gln Arg Arg
 1               5

<210> SEQ ID NO 6
<211> LENGTH: 16
<212> TYPE: PRT
<213> ORGANISM: Drosophila melanogaster

<400> SEQUENCE: 6

Arg Gln Ile Lys Ile Trp Phe Pro Asn Arg Arg Met Lys Trp Lys Lys
 1               5                  10                  15

<210> SEQ ID NO 7
<211> LENGTH: 9
<212> TYPE: PRT
<213> ORGANISM: Human papilloma virus

<400> SEQUENCE: 7

Arg Ala His Tyr Asn Ile Val Thr Phe
 1               5

<210> SEQ ID NO 8
<211> LENGTH: 9
<212> TYPE: PRT
<213> ORGANISM: Mus musculus

<400> SEQUENCE: 8

Ser Val Tyr Asp Phe Phe Val Trp Leu
 1               5

<210> SEQ ID NO 9
<211> LENGTH: 10
<212> TYPE: PRT
<213> ORGANISM: Theiler's murine encephalomyelitis virus

<400> SEQUENCE: 9

Phe His Ala Gly Ser Leu Leu Val Phe Met
 1               5                  10

<210> SEQ ID NO 10
<211> LENGTH: 8
<212> TYPE: PRT
<213> ORGANISM: Gallus gallus domesticus

<400> SEQUENCE: 10

Ser Ile Ile Asn Phe Glu Lys Leu
 1               5

<210> SEQ ID NO 11
<211> LENGTH: 8
<212> TYPE: PRT
<213> ORGANISM: Gallus gallus domesticus

<400> SEQUENCE: 11

Lys Val Val Arg Phe Asp Lys Leu
 1               5

<210> SEQ ID NO 12
<211> LENGTH: 9
<212> TYPE: PRT
```

```
<213> ORGANISM: Mus musculus

<400> SEQUENCE: 12

Leu Pro Tyr Leu Gly Trp Leu Val Phe
 1               5
```